(12) United States Patent
Ishikawa et al.

(10) Patent No.: US 11,331,225 B2
(45) Date of Patent: May 17, 2022

(54) STRETCHABLE STRUCTURE OF DISPOSABLE WEARING ARTICLE AND METHOD OF FORMING THE SAME

(71) Applicant: DAIO PAPER CORPORATION, Ehime (JP)

(72) Inventors: Yoshitake Ishikawa, Ehime (JP); Yosuke Mori, Ehime (JP)

(73) Assignee: Daio Paper Corporation, Ehime (JP)

( * ) Notice: Subject to any disclaimer, the term of this patent is extended or adjusted under 35 U.S.C. 154(b) by 528 days.

(21) Appl. No.: 16/333,787

(22) PCT Filed: May 11, 2017

(86) PCT No.: PCT/JP2017/017812
§ 371 (c)(1),
(2) Date: Mar. 15, 2019

(87) PCT Pub. No.: WO2018/061288
PCT Pub. Date: Apr. 5, 2018

(65) Prior Publication Data
US 2019/0254881 A1    Aug. 22, 2019

(30) Foreign Application Priority Data
Sep. 30, 2016    (JP) .............................. JP2016-193526

(51) Int. Cl.
*A61F 13/15* (2006.01)
*A61F 13/49* (2006.01)
(Continued)

(52) U.S. Cl.
CPC ........ *A61F 13/15739* (2013.01); *A61F 13/15* (2013.01); *A61F 13/49* (2013.01);
(Continued)

(58) Field of Classification Search
CPC .......... A61F 13/15739; A61F 13/49019; A61F 13/4902; Y10T 156/1057; B29C 65/74
See application file for complete search history.

(56) References Cited

U.S. PATENT DOCUMENTS

2017/0209314 A1    7/2017   Ishikawa et al.

FOREIGN PATENT DOCUMENTS

| EP | 3437601 | 2/2019 |
|---|---|---|
| JP | 2004-229857 | 8/2004 |

(Continued)

OTHER PUBLICATIONS

International Search Report, PCT/JP2017/017812, dated Jun. 27, 2017.

*Primary Examiner* — George R Koch
*Assistant Examiner* — Christopher C Caillouet
(74) *Attorney, Agent, or Firm* — Andrus Intellectual Property Law, LLP

(57) ABSTRACT

A stretchable structure is provided with an elastic member provided between a first sheet layer and a second sheet layer. A stretchable region and a non-stretchable region are alternatively repeated three or more regions from end to end in the stretching direction of the stretchable structure. Both ends are the stretchable region. Both of the ends have an adhesive region of a hot melt adhesive, where the elastic member is adhered to the first sheet layer and the second sheet layer, in a spread state, intervals between adhesive regions adjacent in the stretching direction are all the same, twice of a stretching direction length of the adhesive region positioned on both ends in the stretching direction of the stretchable structure and a stretching direction length of the adhesive region positioned at an end portion on the non-stretchable region side of the stretchable region are all the same.

8 Claims, 25 Drawing Sheets

(51) Int. Cl.
*A61F 13/496* (2006.01)
*B29C 65/48* (2006.01)
*B29C 65/74* (2006.01)
*A61F 13/64* (2006.01)
*B29L 31/48* (2006.01)

(52) U.S. Cl.
CPC ...... *A61F 13/496* (2013.01); *A61F 13/49019* (2013.01); *A61F 13/64* (2013.01); *B29C 65/4815* (2013.01); *B29C 65/74* (2013.01); *B29L 2031/4878* (2013.01)

(56) References Cited

FOREIGN PATENT DOCUMENTS

| | | |
|---|---|---|
| JP | 2008-295930 | 12/2008 |
| JP | 2009-148447 | 7/2009 |
| JP | 2009-297096 | 12/2009 |
| JP | 2013-132331 | 7/2013 |
| JP | 2015-226569 | 12/2015 |
| JP | 5997404 | 10/2017 |
| WO | 2015137128 | 9/2015 |
| WO | 2015/199186 | 12/2015 |

(a)

(b)

(c)

STRETCHABLE STRUCTURE OF DISPOSABLE WEARING ARTICLE AND METHOD OF FORMING THE SAME

CROSS-REFERENCE TO RELATED APPLICATIONS

This application is the U.S. national stage application of International Application PCT/JP2017/017812, filed May 11, 2017, which international application was published on Apr. 5, 2018, as International Publication WO 2018/061288 in the Japanese language. The International Application claims priority of Japanese Patent Application No. 2016-193526, filed Sep. 30, 2016. The international application and Japanese application are both incorporated herein by reference, in entirety.

TECHNICAL FIELD

The present invention relates to a stretchable structure of a disposable wearing article and a method of forming the same.

BACKGROUND ART

In general, a stretchable structure is provided in disposable wearing articles to improve fitting property of each part. For example, in disposable diapers of an underpants-type or a tape-type, it has been widely practiced to provide the stretchable structure in a lower torso portion along the circumferential direction thereof or to provide the stretchable structure in leg portions along the circumferential direction thereof. Further, it has been widely practiced to provide the stretchable structure in the front-back direction called a "three-dimensional gather" and a "planer gather" for general disposable wearing articles including sanitary napkins, disposable swimsuits, and disposable diaper covers as well as disposable diapers of an underpants-type and a tape type (refer to, for example, Patent Literatures 1 to 5).

A representative example of the stretchable structure of such a disposable wearing article includes a first sheet layer, a second sheet layer opposed to one surface of the first sheet layer, and a plurality of elongated elastic members provided at intervals therebetween along a stretching direction between the first sheet layer and the second sheet layer. The first sheet layer and the second sheet layer play roles of forming a planar stretchable region and also covering and concealing the elastic member. The elastic members incorporated between the first sheet layer and the second sheet layer play a role of generating an elastically stretchable force. The elastic members are fixed to the first sheet layer and the second sheet layer at least at both ends of the stretchable region in a state of being stretched in the stretching direction. By this fixing, the elastic members, the first sheet layer, and the second sheet layer are integrated, and the first sheet layer and the second sheet layer are contracted due to a contracting force of the elastic members to form pleats and wrinkles. In addition, when this contraction state is stretched against the contraction force of the elastic members, the pleats and wrinkles are spread. Normally, the sheet layer is in a spread state without pleats and wrinkles at the elastic elongation limit, and the pleats are formed as the elastic members contract, and in a natural length state, the pleats are closest to each other. At the present time, as a means for fixing the elastic member to the first sheet layer and the second sheet layer, in most cases, a hot melt adhesive is selected.

In addition, the first sheet layer and the second sheet layer are intermittently or continuously bonded to each other in at least one of the stretching direction and the direction orthogonal thereto. This is because when there is almost no bonding between the first sheet layer and the second sheet layer, one largely lifts or shifts from the other, such that the appearance and the wearing feeling deteriorate. The bonding form of the first sheet layer and the second sheet layer is roughly divided into a shared form (refer to Patent Literatures 1 to 3), in which the first sheet layer and the second sheet layer are bonded to each other via a hot melt adhesive at a position where at least the elastic members pass at the same time as fixing the elastic member to the first sheet layer and the second sheet layer, and an independent form (refer to Patent Literatures 4 and 5), in which the first sheet layer and the second sheet layer are bonded together by welding such as ultrasonic welding at positions other than the position where the elastic members pass instead of fixing the elastic member to the first sheet layer and the second sheet layer.

On the other hand, in disposable wearing articles, even when elasticity is imparted only to an arbitrary part, in order to facilitate manufacturing, after attaching the elastic members continuously to the article in the stretching direction, the non-stretchable region unnecessary to stretching is processed into a state in which a contraction force by the elastic members does not act (hereinafter, also referred to as "stretchability is killed"). For example, in the case of imparting stretchability in the width direction around the waist of an underpants-type disposable diaper, it has been widely practiced that, after attaching the elongated elastic members over the entire width direction, a central portion in the width direction overlapping with an absorber is cut finely, the stretchability of the portion is killed, and regions on both sides in the width direction is a stretchable region.

At the time of manufacture, generally, while continuously conveying the first sheet layer and the second sheet layer in the machine direction (MD), elongated elastic members are continuously sandwiched between the first sheet layer and the second sheet layer, the first sheet layer and the second sheet layer are bonded to each other, and the elastic members are fixed to at least one of the first sheet layer and the second sheet layer, the elastic members are cut at a position in the MD which is a non-stretchable region, then an inner member is attached, a front body and a back body are adhered, and cutting at the boundary between individual products is performed.

Here, when elastic members at both ends in the stretching direction of the stretchable region are fixed with a hot melt adhesive, for example, as illustrated in FIG. 21, prior to bonding of a first sheet layer 12S and a second sheet layer 12H, a hot melt adhesive 71 is applied to at least one of elastic members 19, the first sheet layer 12S, and the second sheet layer 12H. Then, the first sheet layer 12S and the second sheet layer 12H are bonded to each other, and the elastic member 19 is bonded to at least one of the first sheet layer 12S and the second sheet layer 12H via the hot melt adhesive 71. In order to efficiently apply the hot melt adhesive 71, applying steps to a first application region 111 covering both sides in the MD of a boundary 101 between parts to be individual products, a second application region 112 adjacent to a boundary 102 changing from a stretchable region 22 to a non-stretchable region 21 on the stretchable region 22 side, a third application region 113 adjacent to a boundary 103 changing from the non-stretchable region 21 to the stretchable region 22 on the stretchable region 22, 23 side are defined as one cycle, and a hot melt adhesive is repeatedly applied in the MD starting from any one of the application regions 111 to 113 in one cycle.

However, as illustrated in FIG. 21(a), a conventional product has the following problems. That is, an interval 71d in the MD (stretching direction) between the first application region 111 and the second application region 112, which are positioned at both ends in the stretching direction of the stretchable region 22, an interval 71d in the MD (stretching direction) between the third application region 113 and the first application region 111, and an interval 71d in the MD between the second application region 112 and the third application region 113 positioned on both sides in the width direction of the non-stretchable region 21 are slightly different, and an MD direction dimension 71w of the first application region 111, an MD direction dimension 71w of the second application region 112, and an MD direction dimension 71w of the third application region 113 are slightly different from each other.

That is, as illustrated in FIGS. 21(b) and 21(c), in positioning of application sites of a hot melt adhesive at the starting time of manufacturing equipment, if an application region to be a starting point is erroneously set, the application sites of the hot melt adhesive 71 with respect to a cutting position CT of the elastic members 19 are shifted to one side in the MD depending on the difference in the intervals 71d between the respective application regions 111 to 113 and the difference in the MD direction dimensions 71w. In particular, in general underpants-type disposable diapers, since the difference in the intervals between the respective application regions and the difference in the MD direction dimensions are small, it is easy to erroneously set the application region to be the starting point, and it is difficult to find the error. In this respect, manufacturing is difficult. Incidentally, the state indicated in FIG. 21(b) illustrates a state in which the position of the first application region 111 is erroneously set to the position of the second application region 112. The state indicated in FIG. 21(c) illustrates a state in which the position of the first application region 111 is erroneously set to the position of the third application region 113.

CITATION LIST

Patent Literature

Patent Literature 1: JP 2004-229857 A
Patent Literature 2: JP 2013-132331 A
Patent Literature 3: JP 2009-148447 A
Patent Literature 4: JP 2008-295930 A
Patent Literature 5: JP 2009-297096 A

SUMMARY OF INVENTION

Technical Problem

The main object of the present invention is to facilitate manufacturing of a stretchable structure using an elastic member.

Solution to Problem

The present invention that has solved the above problem will be described below.
<First Aspect>
A stretchable structure of a disposable wearing article, the disposable wearing article including a first sheet layer, a second sheet layer opposed to one surface of the first sheet layer, and an elastic member provided between the first sheet layer and the second sheet layer, wherein, a stretchable region and a non-stretchable region are alternately repeated to form three or more regions from one end to the other end in a stretching direction in the stretchable structure, the both ends of the three or more regions being the stretchable regions, an adhesive region of a hot melt adhesive, where the elastic member is adhered to at least one of the first sheet layer and the second sheet layer, is provided at both ends of the stretchable region in the stretching direction, and in a spread state, intervals between adhesive regions adjacent in the stretching direction are all the same, and twice of a length in the stretching direction of the adhesive region positioned at both ends in the stretching direction of the stretchable structure, and a stretching direction length of the adhesive region positioned at an end portion on the non-stretchable region side of the stretchable region are all the same.

(Function and Effect)

According to the present aspect, at the time of manufacture, since the intervals of the application regions of the hot melt adhesive for forming respective adhesive regions and the dimensions in the stretching direction of respective application regions are all the same. Therefore, in positioning of application positions of the hot melt adhesive at the starting time of manufacturing equipment, in principle, there is no situation in which the application region to be a starting point is erroneously set. That is, for example, as in the case of the above-described underpants-type disposable diaper, in the case where the hot melt adhesive is applied to the first application region, the second application region, and the third application region as one cycle, if the intervals between respective application regions and the MD direction dimensions (stretching direction dimension) are the same, the application region to be a starting point is not necessarily distinguished. For that reason, even if any application region is designated as the starting point, the hot melt adhesive can be reliably applied to a predetermined position with respect to cutting positions of the elastic member. Therefore, the application site of the hot melt adhesive at the starting time of the manufacturing equipment is not erroneously positioned, and it makes manufacturing very easy.

<Second Aspect>

In the stretchable structure of a disposable wearing article according to the first aspect, the disposable wearing article is an underpants-type disposable diaper ii which includes an outer member forming a front body and a back body and an inner member attached to the outer member and containing an absorber, and in which both sides of the outer member in the frond body and both sides of the outer member of the back body are joined to each other, a range in a front-back direction corresponding to the joined portion is an annular lower torso portion, and a waist opening and a pair of right and left leg openings are formed, in the stretchable structure, the elastic member is provided along a width direction in a lower torso portion of the outer body, and the non-stretchable region is provided in an intermediate portion in the width direction of the lower torso portion, and the stretchable region is provided on both sides in the width direction of the non-stretchable region.

(Function and Effect)

Thus, the stretchable structure having the stretchable region and the non-stretchable region is suitable for the lower torso portion of the outer member of an underpants-type disposable diaper.

<Third Aspect>

In the stretchable structure of a disposable wearing article according to the first or second aspect, the first sheet layer and the second sheet layer are adhered via a hot melt adhesive intermittently disposed at least in the stretching direction, or no hot melt adhesive is provided between the first sheet layer and the second sheet layer, in a region other than the adhesive region of the hot melt adhesive at both ends in the stretching direction of the stretchable region.

(Function and Effect)

The structure as in the present aspect has high flexibility at portions other than both ends in the stretching direction of the stretchable region. Further, in the structure of the present aspect, since it is important to fix the elastic members at both ends in the stretching direction of the stretchable region, as described above, it is particularly important that a hot melt adhesive can be reliably applied to a predetermined position with respect to cutting positions of the elastic member.

<Fourth Aspect>

A method of forming a stretchable structure of a disposable wearing article, comprising:

while continuously conveying a first sheet layer and a second sheet layer in the MD, an elastic member is continuously sandwiched between the first sheet layer and the second sheet layer in the MD, and fixing the elastic member to at least one of the first sheet layer and the second sheet layer; and after that, repeatedly forming a unit stretchable structure in the machine direction, in which a stretchable region and a non-stretchable region obtained by cutting the elastic member are alternately repeated three or more regions in the MD, and both ends in the MD become stretchable regions, and cutting the unit stretchable structure is cut into individual stretchable structures at the boundary of the unit stretchable structures adjacent in the MD, wherein, when the elastic member is fixed, the elastic member is fixed to at least one of the first sheet layer and the second sheet layer via the hot melt adhesive, in an application region of a hot melt adhesive disposed in each of a portion to be an end portion of a stretchable region of a pair of the unit stretchable structures adjacent in the machine direction and a portion to be an end portion on the non-stretchable region side of the stretchable region, intervals between application regions adjacent in the MD are the same, and the application regions have the same length in the MD.

(Function and Effect)

The same functions and effects as those obtained in the first aspect are obtained.

<Fifth Aspect>

In the method of forming a stretchable structure of a disposable wearing article according to the fourth aspect, the disposable wearing article is an underpants-type disposable diaper which includes an outer member forming a front body and a back body and an inner member attached to the outer member and containing an absorber, and in which both sides of the outer member in the frond body and both sides of the outer member of the back body are joined to each other, a range in a front-back direction corresponding to the joined portion is an annular lower torso portion, and a waist opening and a pair of right and left leg openings are formed, in the stretchable structure, the elastic member is provided along a width direction in a lower torso portion of the outer member, and the non-stretchable region is provided in an intermediate portion in the width direction of the lower torso portion, and the stretchable region is provided on both sides in the width direction of the non-stretchable region.

(Function and Effect)

The same functions and effects as those obtained in the second aspect are obtained.

<Sixth Aspect>

In the method of forming a stretchable structure of a disposable wearing article according to the fourth or fifth aspect, the first sheet layer and the second sheet layer are adhered via a hot melt adhesive intermittently in the MD, or no hot melt adhesive is applied between the first sheet layer and the second sheet layer in a region other than an application region of a portion to be an end portion of a stretchable region of a pair of the unit stretchable structures adjacent in the MD and a portion to be an end portion on the non-stretchable region side of the stretchable region.

(Function and Effect)

The same functions and effects as those obtained in the third aspect are obtained.

Advantage Effects of Invention

As described above, according to the present invention, there can be obtained advantages that the stretchable structure is easily manufactured using the elastic member.

DESCRIPTION OF EMBODIMENTS

Hereinafter, embodiments of the present invention will be described in detail with reference to the accompanying drawings.

FIGS. 1 to 7 illustrate an example of an underpants-type disposable diaper. This underpants-type disposable diaper is composed of an outer member 12 forming the outer surface (back side) of the diaper and an inner member 200 attached to the outer member 12. The reference sign 201 denotes a joining region between the inner member 200 and the outer member 12. The reference sign Y denotes the maximum length of the diaper. The reference sign X denotes the maximum width of the diaper.

The inner member 200 is a portion for absorbing and hold excrement such as urine, and the outer member 12 is a portion for attaching the inner member 200 to the body. In addition, the dotted portions in the cross-sectional view indicate the joint portion to join each constituent member and are formed by solid coating, bead coating, curtain coating, summit coating, or spiral coating of a hot melt adhesive.

(Inner Member)

Figure 3:
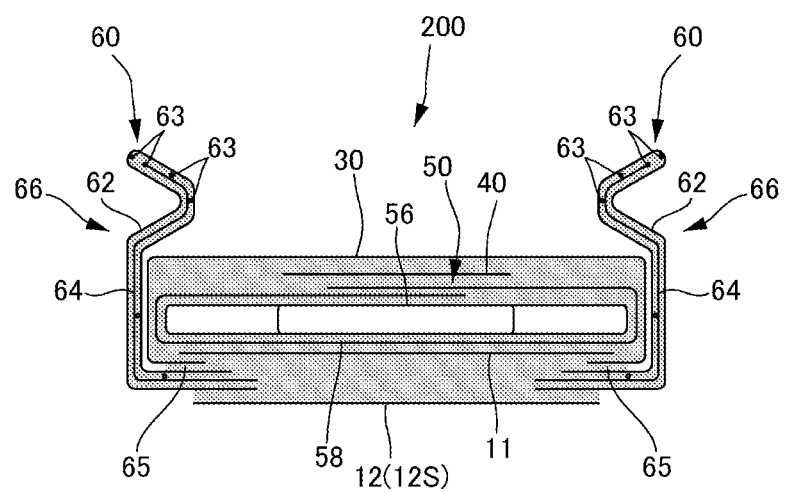
FIG. 3 is a cross-sectional view taken along line 3-3 in FIG. 1.
Figure 4:
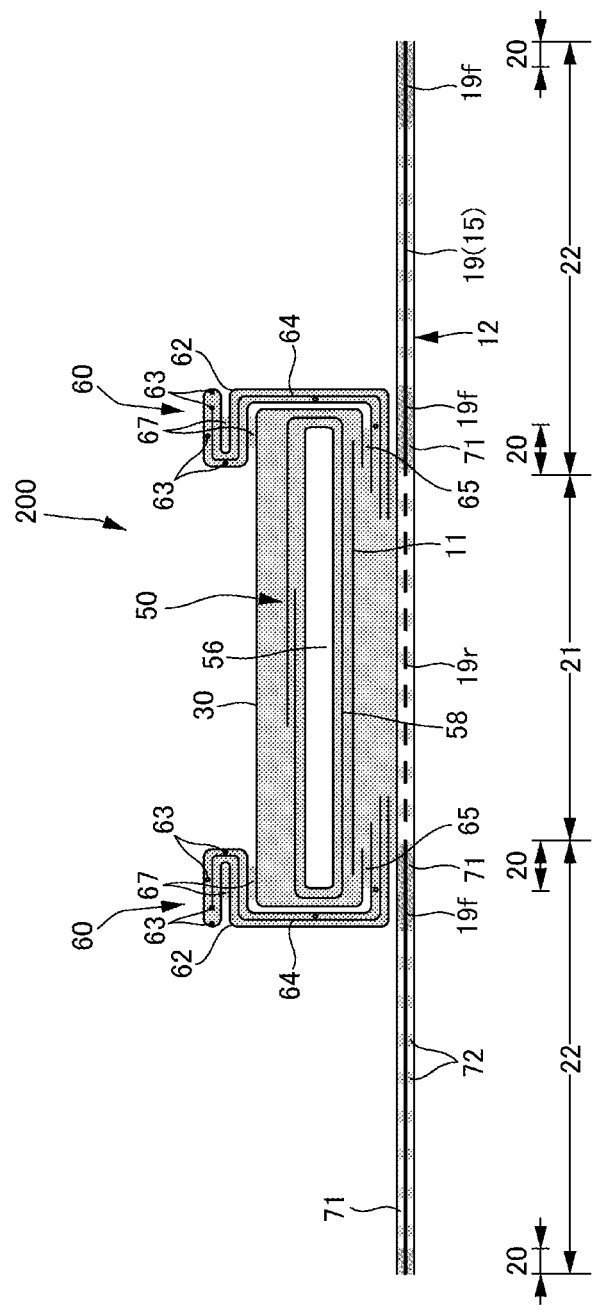
FIG. 4 is a cross-sectional view taken along line 4-4 in FIG. 1.
Figure 5:
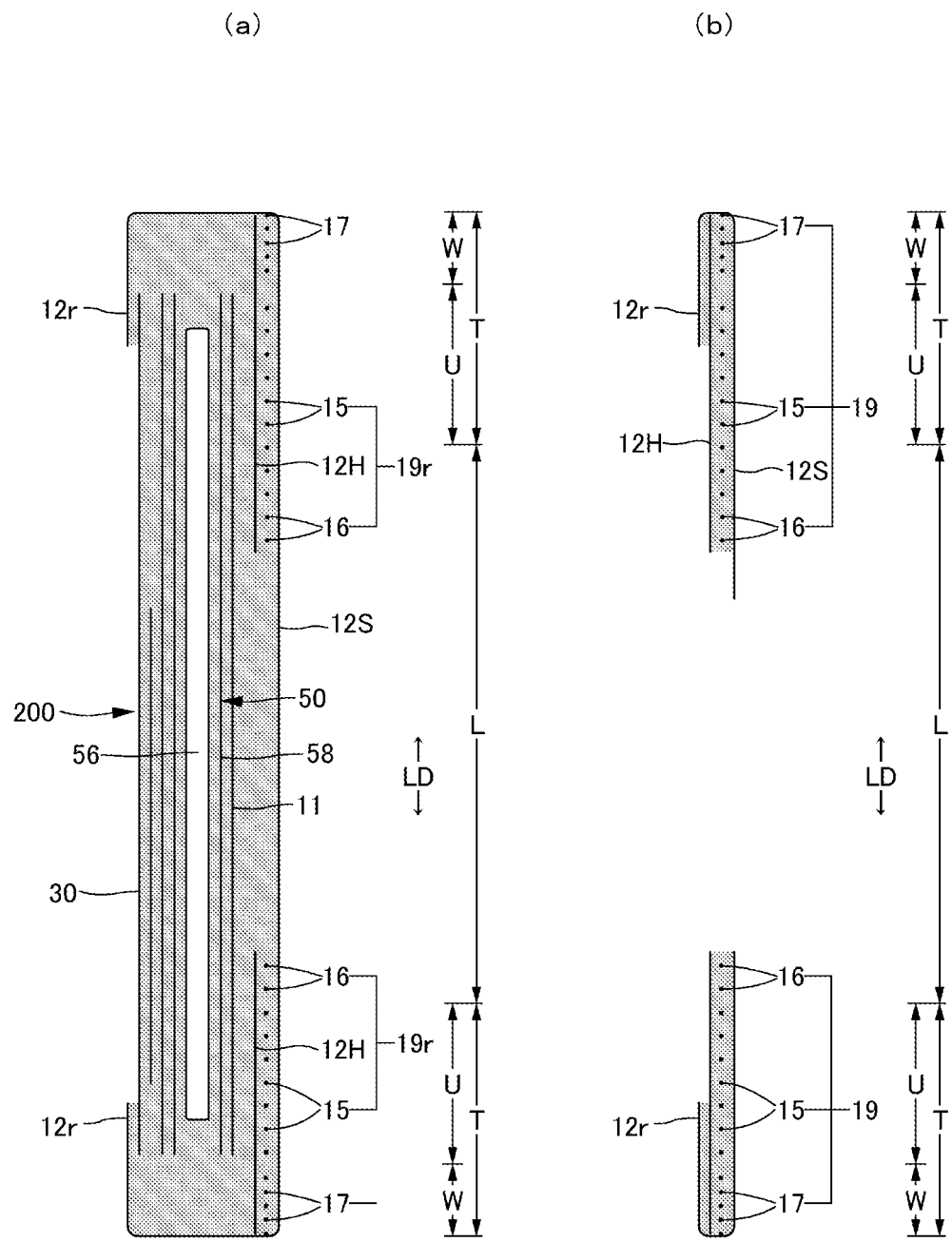
FIG. 5(a) is a cross-sectional view taken along line 5-5 in FIG. 1.
FIG. 5(b) is a cross-sectional view taken along line 2-2 in FIG. 1.

The inner member 200 can have an arbitrary shape, but in the illustrated form, it is rectangular. As illustrated in FIGS. 3 to 5, the inner member 200 is provided with a top sheet 30 which is in contact with the skin, a liquid impervious sheet 11, and an absorbent element 50 interposed therebetween, and is a main unit section that plays a role of an absorbing function. The reference sign 40 denotes an intermediate sheet (second sheet) provided between the top sheet 30 and the absorbent element 50 in order to promptly transfer liquid permeated through the top sheet 30 to the absorbent element 50. The reference sign 60 denotes a three-dimensional gather 60 provided on both sides of the inner member 200 and standing on the skin side of a wearer in order to prevent excrement from leaking to both sides of the inner member 200.

(Top Sheet)

The top sheet 30 has a property of permeating liquid, and examples of the top sheet 30 include a porous or nonporous nonwoven fabric and a porous plastic sheet. Among them, a raw fiber of the nonwoven fabric is not particularly limited. Examples of the raw fiber include synthetic fibers such as polyolefin such as polyethylene and polypropylene, polyester, and polyamide, regenerated fibers such as rayon and cupra, natural fibers such as cotton, and mixed fibers or composite fibers in which two or more of these are used. Further, the nonwoven fabric may be manufactured by any processing. Examples of the processing method include known methods such as a spun lace method, a spunbond method, a thermal bond method, a melt blown method, a needle punch method, an air-through method, and a point bond method. For example, if flexibility and drapeability are required, the spunbond method and the spun lace method are preferable processing methods, and if bulkiness and softness are required, the air-through method, the point bond method, and the thermal bond method are preferable processing methods.

Further, the top sheet 30 may be made of single layer sheet or a laminated sheet obtained by bonding two or more sheets. Similarly, the top sheet 30 may be composed of one sheet or two or more sheets with respect to the plane direction.

In the case of providing the three-dimensional gather 60, it is preferable that both sides of the top sheet 30 are disposed around the back side of the absorbent element 50 through a space between the liquid impervious sheet 11 and the three-dimensional gather 60, and the both sides are adhered to the liquid impervious sheet 11 and the three-dimensional gather 60 with a hot melt adhesive or the like to prevent liquid permeation.

(Intermediate Sheet)

An intermediate sheet (also called a "second sheet") 40 can be provided between the top sheet 30 and the absorbent element 50. This intermediate sheet 40 not only improves the absorption performance by an absorber 56 by immediately moving liquid to the absorber 56 side, but also prevents the absorbent liquid from returning from the absorber 56 and makes the surface of the top sheet 30 dry texture. The intermediate sheet 40 can also be omitted.

Examples of the intermediate sheet 40 include the same material as the top sheet 30, a spun lace, a spunbond, SMS, a pulp nonwoven fabric, a mixed sheet of pulp and rayon, a point bond, or a crepe paper. In particular, an air-through nonwoven fabric is preferable because it is bulky. It is preferable to use a composite fiber having a core-sheath structure for the air-through nonwoven fabric. In this case, a resin used for the core may be polypropylene (PP), but polyester (PET) having high rigidity is preferable. The basis weight is preferably 20 to 80 g/m$^2$, more preferably 25 to 60 g/m$^2$. The fineness of the raw fiber of the nonwoven fabric is preferably 2.2 to 10 dtex. To increase the bulkiness of the nonwoven fabric, it is also preferable to use eccentric fibers whose core is not in the center, hollow fibers, eccentric and hollow fibers, as mixed fibers of all or a part of the raw fibers.

The intermediate sheet 40 in the illustrated form is disposed at the center shorter than the width of the absorber 56, but may be provided over the maximum width. The length of the intermediate sheet 40 in the longitudinal direction may be the same as the length of the absorber 56 or may be within a short length range centered on the liquid receiving area.

(Liquid Impervious Sheet)

The material of the liquid impervious sheet 11 is not particularly limited, but examples of the material include a plastic film made of an olefin resin such as polyethylene and polypropylene, a laminated nonwoven fabric having a plastic film on the surface of a nonwoven fabric, and a laminated sheet obtained by joining a nonwoven fabric or the like on a plastic film. As the liquid impervious sheet 11, it is preferable to use a material having liquid impermeability and moisture permeability that has been favorably used in recent years from the viewpoint of prevention of stuffiness. As the moisture-permeable plastic film, a microporous plastic film is widely used. The microporous plastic film is obtained by stretching a sheet in a monoaxial or biaxial direction after molding the sheet obtained by mixing and kneading an inorganic filler and polyolefin resin such as polyethylene or polypropylene. In addition to this, a nonwoven fabric using a micro-denier fiber and a liquid impervious sheet without a plastic film having an increased leakage resistance obtained by applying heat and pressure to reduce the gaps between fibers or by coating with highly water-absorbing resin, a hydrophobic resin; or a water repellent agent can also be used as the liquid impervious sheet 11.

To enhance leakage resistance, the liquid impervious sheet 11 can also be disposed around the both sides of the absorbent element 50 to extend to the both sides of the side surface of the top sheet 30 of the absorbent element 50.

Further, an excretion indicator that changes its color due to absorption of a liquid component can be provided on the inside of the liquid impervious sheet 11, in particular, on the side surface of the absorber 56.

(Three-Dimensional Gather)

The three-dimensional gather 60 is strip-shaped members extending along the both sides of the inner member 200 in the front-back direction. The three-dimensional gather 60 is provided to block fluid excretion (urine, loose stools, etc.) moving on the top sheet 30 in the lateral direction and prevent lateral leakage. The three-dimensional gather 60 according to the present embodiment is provided so as to stand upright from the side portion of the inner member 200, the root-side portion stands obliquely toward the center-side in the width direction, and the portion closer to the tip side than the intermediate portion stands obliquely toward the outside in the width direction. Although the three-dimensional gather of this embodiment is of a surface contact type, a line contact type three-dimensional gather (not illustrated) which is not folded back outward in the width direction can also be used.

To be more specific, the three-dimensional gather 60 is formed by folding in two, in the width direction, a belt shaped gather sheet 62 having a length equal to the front-back direction length of the inner member 200, and fixing a plurality of elongated elastic members 63 with intervals in the width direction in an extended state along the longitudinal direction between the folded back portion and an adjacent sheet. An end portion on the opposite side to the folded back portion in the width direction in the three-dimensional gather 60 is an attachment portion 65 fixed to the rear surface of the side edge portion of the inner member 200. A portion other than the attachment portion 65 is a protruding portion 66 (a portion on the folded back portion side) protruding from the attachment portion 65. The both ends of the protruding portion 66 in the front-back direction are extended from the attachment portion 65 to the side surface of the top sheet 30 through the side portion of the inner member 200, and also the both ends are a fallen part fixed by a fixing means such as the hot melt adhesive 67 to the side surface of the top sheet 30. The intermediate portion in the front-back direction of the protruding portion 66 is a non-fixed free portion, and the elongated elastic member 63 along the front-back direction is fixed to the free portion in an extended state at least over the entire front-back direction.

As the gather sheet 62, a nonwoven fabric which is flexible and excellent in uniformity and concealing property such as a spunbonded nonwoven fabric (SS, SSS, etc.), SMS nonwoven fabric (SMS, SSMMS, etc.), and meltblown nonwoven fabric can be preferably used. The nonwoven fabric may be water-repellent treated using silicone as necessary. The fiber basis weight is preferably set to about 10 to 30 g/m$^2$. As the elongated elastic member 63, such as a rubber thread can be used. When a spandex rubber thread is used, the fineness is preferably 470 to 1240 dtex, more preferably 620 to 940 dtex. The stretch rate at the time of fixing is preferably from 150 to 350%, more preferably from 200 to 300%. The term "stretch rate" means a value when the natural length is taken as 100%. As illustrated in the drawing, a waterproof film 64 may be interposed between the gather sheets folded in two.

The number of the elongated elastic members 63 provided in the free portion of the three-dimensional gather 60 is preferably two to six, more preferably three to five. An appropriate arrangement interval 60$d$ is 3 to 10 mm With such a configuration, the three-dimensional gather 60 easily comes into surface contact with the skin in a range in which the elongated elastic member 63 is disposed. The elongated elastic member 63 may be disposed not only on the tip side but also on the root side.

The fixing target of the attachment portion 65 of the three-dimensional gather 60 can be an appropriate member such as the top sheet 30, the liquid impervious sheet 11, and the absorbent element 50 in the inner member 200.

In the three-dimensional gather 60 formed as described above, a contraction force of the elongated elastic members 63 acts so as to bring both ends in the front-back direction close to each other, but both ends in the front-back direction of the protruding portions 66 are fixed in a fallen state, and a space between the both ends is a non-fixed free portion. Therefore, only the free portion stands so as to come into contact with the body side as illustrated in FIG. 3. Particularly, when the attachment portion 65 is positioned on the back side of the inner member 200, the three-dimensional gathers 60 stand up so as to open outward in the width direction at and around a crotch portion, such that the three-dimensional gathers 60 come into surface contact with a leg portion, and therefore the fitness is improved.

Unlike the illustrated form, three-dimensional gathers can be doubly (in two rows) provided on each of the left and right sides of the inner member 200.

(Absorbent Element)

The absorbent element 50 has the absorber 56 and a package sheet 58 packaging the entire absorber 56. The package sheet 58 can also be omitted.

(Absorber)

The absorber 56 can be formed of an assembly of fibers. As this fiber assembly, besides those obtained by stacking short fibers such as fluff pulp and synthetic fibers, a filament assembly obtained by opening tows (fiber bundles) of synthetic fibers such as cellulose acetate as required can also be used. When fluff pulp or short fibers are stacked, fiber basis weight can be set to, for example, about 100 to 300 g/m², and in the case of a filament assembly, fiber basis weight can be set to about 30 to 120 g/m². The fineness of a synthetic fiber is, for example, 1 to 16 dtex, preferably 1 to 10 dtex, more preferably 1 to 5 dtex. In the case of filament assembly, the filaments may be non-crimped fibers, but are preferably crimped fibers. The degree of crimp of the crimped fiber can be, for example, about 5 to 75 per inch, preferably 10 to 50 per inch, and more preferably about 15 to 50 per inch. In addition, crimped fibers which are uniformly crimped are often used. It is preferable to disperse and hold the high absorbent polymer particles in the absorber 56.

Figure 1:
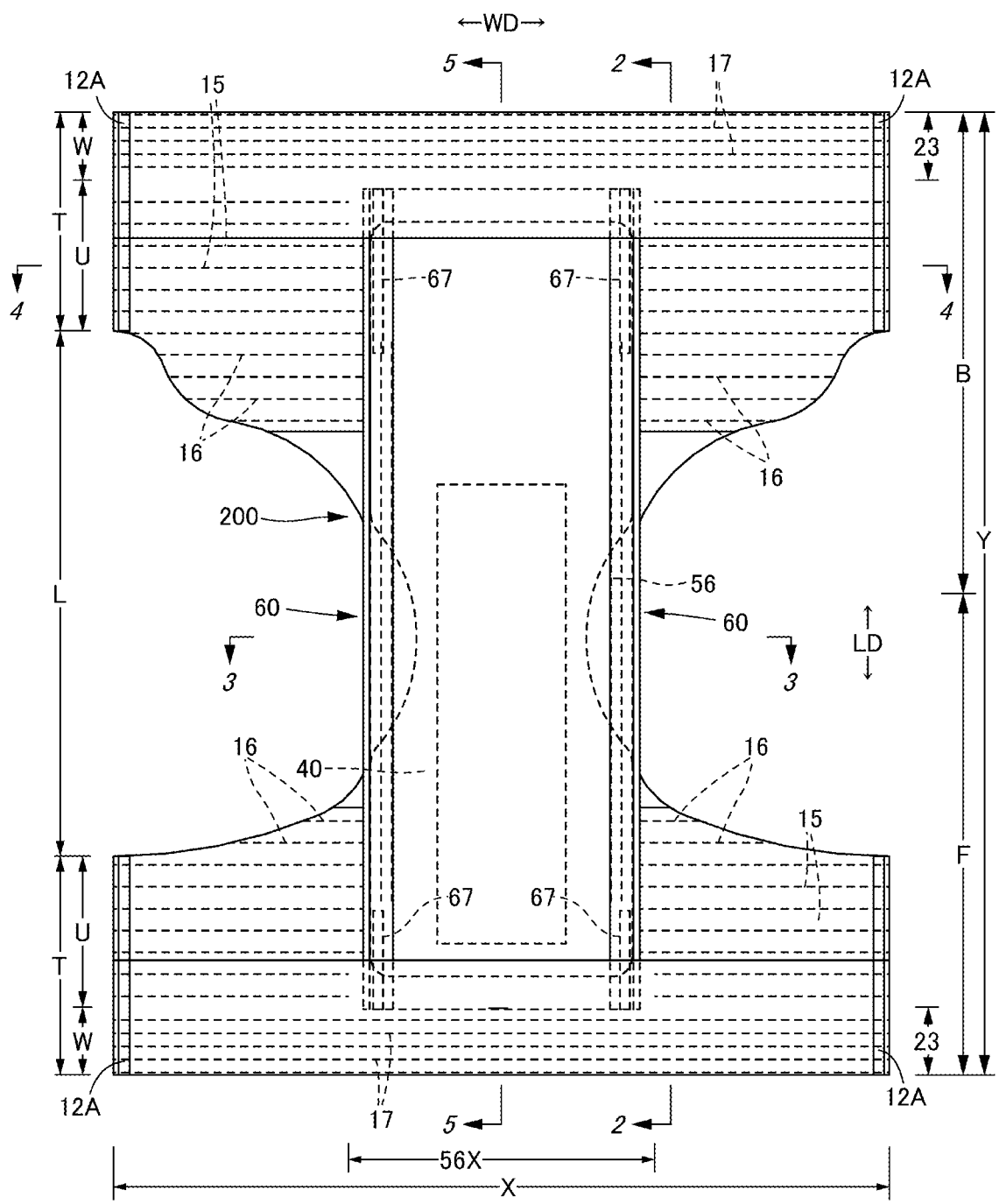
FIG. 1 is a plan view illustrating the inner surface of an underpants-type disposable diaper in a state where a diaper is spread.
Figure 2:
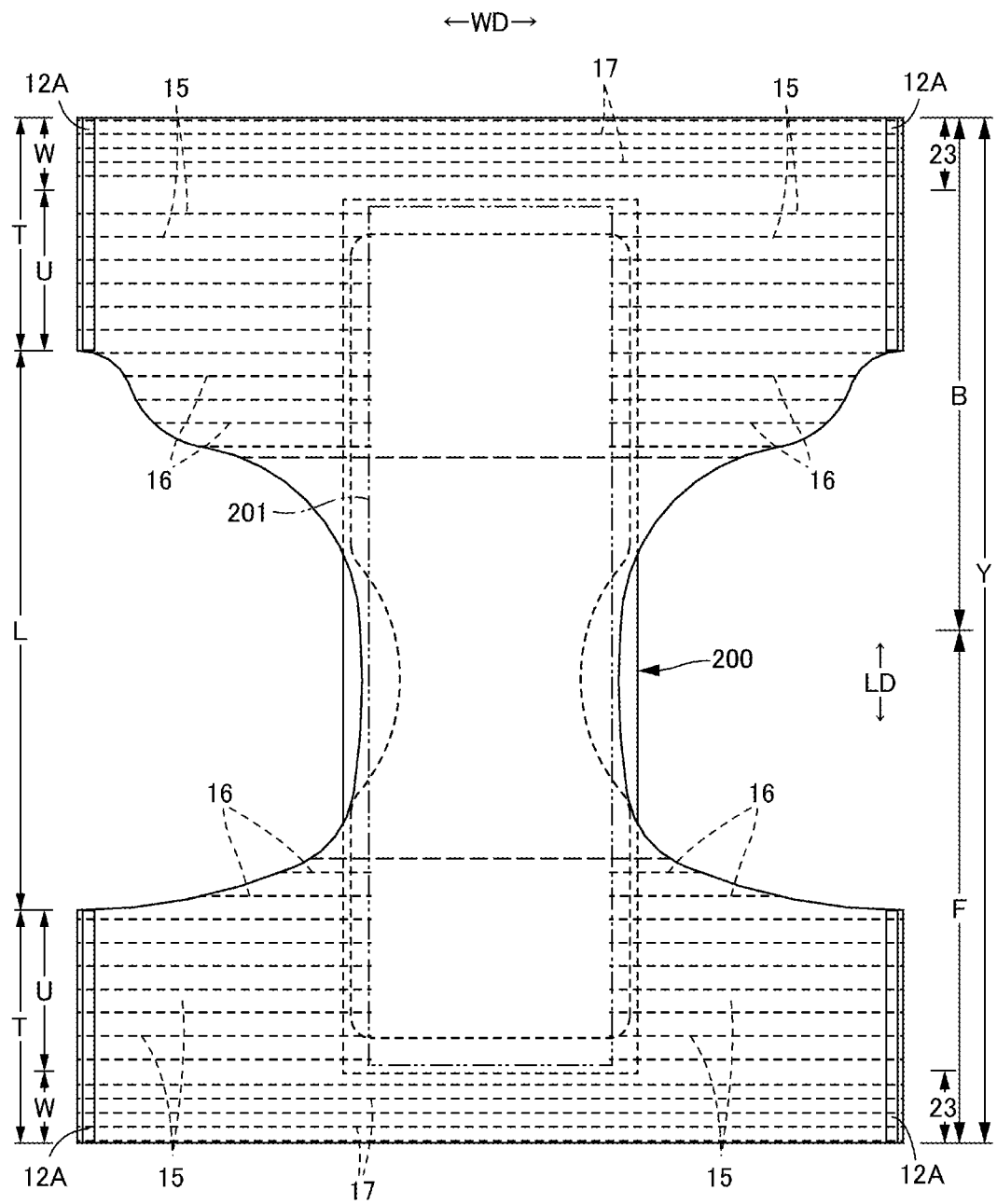
FIG. 2 is a plan view illustrating the outer surface of an underpants-type disposable diaper in a state where a diaper is spread.

The absorber 56 may have a rectangular shape, and, as illustrated in FIGS. 1 and 2, preferably has an hourglass-shape having a front end portion, a back end portion, and a constricted portion positioned between the front end portion and the back end portion and having narrower width than those of the front end portion and the back end portion, since the fitness of the absorber 56 itself and the three-dimensional gather 60 around the legs is improved.

Further, although the size of the absorber 56 can be appropriately determined, it is preferable that the absorber 56 extends to or near the peripheral edge portion of the inner member in the front-back direction and the width direction. The reference sign 56X denotes the width of the absorber 56.

(High Absorbent Polymer Particle)

The absorber 56 can contain high absorbent polymer particles partially or entirely. The high absorbent polymer particles mean "powder" in addition to "particles". The high absorbent polymer particles have a particle diameter that can be used in this type of disposable wearing articles and is desirably 1000 μm or less, in particular, 150 to 400 μm. The material of the high absorbent polymer particles is not particularly limited, but materials having a water absorption capacity of 40 g/g or more are suitable. Examples of the material of the high absorbent polymer particles include starch-based polymer, cellulose-based polymer, and synthetic polymer, and starch-acrylic acid (salt) graft copolymers, saponified starch-acrylonitrile copolymers, cross-linked sodium carboxymethylcellulose, and acrylic acid (salt) polymers can be used. As the shape of the high absorbent polymer particles, powder and granular particles which are usually used are preferable, but other shapes can also be used.

The high absorbent polymer particles having a water absorption rate of 40 seconds or less are preferably used. When the water absorption rate exceeds 40 seconds, the liquid supplied into the absorber 56 tends to easily return to the outside of the absorber 56.

As the high absorbent polymer particles, those having a gel strength of 1,000 Pa or more are preferably used. This makes it possible to effectively suppress the sticky feeling after absorbing the liquid even in a bulky absorber 56.

The basis weight of the high-absorbent polymer particles can be appropriately determined according to the absorption amount required for the use of the absorber 56. Therefore, although it cannot be said unconditionally, the basis weight can be 50 to 350 g/m². When the basis weight of the polymer is less than 50 g/m², it is difficult to ensure the absorption amount. When it exceeds 350 g/m², the effect is saturated.

If necessary, a spraying density or a spraying amount of the high absorbent polymer particles can be adjusted in the planar direction of the absorber 56. For example, it is possible to increase the spraying amount in an excretory site of liquid compared to the other sites. When considering the difference between men and women, it is possible to increase the spray density (amount) on the front side for men and to increase the spray density (amount) at the center for women. Further, a portion without polymer can be provided locally (for example, in a spot shape) in the planar direction of the absorber 56.

(Package Sheet)

When the package sheet 58 is used, tissue paper, particularly crepe paper, a nonwoven fabric, a poly lamina nonwoven fabric, a sheet with small openings can be used as the material. In this case, it is desirable that the sheet from which the high absorbent polymer particles do not come off is used. When a nonwoven fabric is used in place of the crepe paper, a hydrophilic SMS nonwoven fabric (SMS, SSMMS, etc.) is particularly suitable, and polypropylene, polyethylene/polypropylene composite material and the like can be used as the material. The basis weight is preferably 5 to 40 g/m², particularly preferably 10 to 30 g/m².

The packaging form of the package sheet 58 can be appropriately determined. However, from the viewpoints of ease of manufacturing and prevention of leakage of highly absorbent polymer particles from the front and back end edges, it is preferable that the package sheet 58 is wound around in a cylindrical shape so as to surround the front and back surfaces and both side surfaces of the absorber 56, the front and back edge portions are protruded from the front and back of the absorber 56, and the protruding portion is collapsed in the front and back direction and joined by a joining means such as a hot melt adhesive.

(Outer Member)

Figure 6:
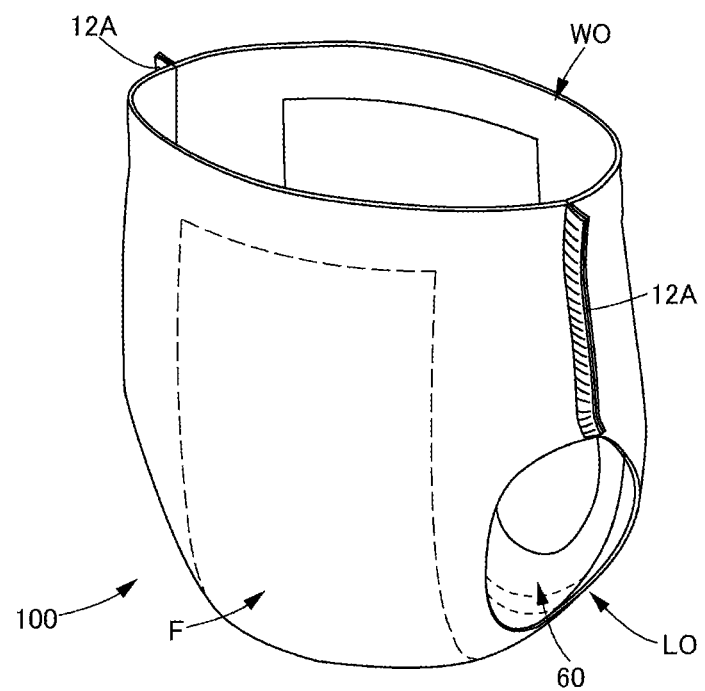
FIG. 6 is a perspective view of an underpants-type disposable diaper.

The outer member 12 has a portion forming a front body F extending from the center in the front-back direction to the ventral side and a portion forming a back body B extending from the center in the front-back direction to the dorsal side. Both sides of the front body F and both sides of the back body B are joined to each other to form a waist opening WO through which the torso of a wearer passes and a pair of left and right leg openings LO through which the legs are passed, as illustrated in FIG. 6. The reference sign 12A denotes a joint portion (hereinafter, this portion is also referred to as a "side seal portion"). The crotch portion means the center in the front-back direction from the waist edge of the front body F to the waist edge of the back body B of a disposable diaper in an unfolded state, and the front side portion and the back side portion from the center mean the front body F and the back body B, respectively.

The outer member 12 has a lower torso portion T and an intermediate portion L. The lower torso portion T is defined as a range in the front-back direction from the waist opening WO to the upper end of the leg opening LO. The intermediate portion L is defined as a range in the front-back direction of a portion forming the leg opening LO (between the region in the front-back direction having a side seal portion 12A of the front body F and the region in the front-back direction having a side seal portion 12A of the back body B). The lower torso portion T can be conceptually divided into a waist portion W which forms an edge portion of the waist opening and a lower torso portion U which is a portion lower than the waist portion W. Normally, when there is a boundary where the width direction stretching stress changes in the lower torso portion T (for example, the fineness and stretch rate of the elastic member change), the region on the waist opening WO side of the boundary closest to the waist opening WO is the waist portion W. When there is no such boundary, the region on the waist opening WO side of the absorber 56 or the inner member 200 is the waist portion W. The length in the longitudinal direction varies depending on the size of a product and can be appropriately determined. For example, the length of the waist portion W can be set to 15 to 40 mm, and the length of the lower waist portion U can be set to 65 to 120 mm. On the other hand, both side edges of the intermediate portion L are constricted along the periphery of the legs of a wearer to form a site for putting the wearer's legs in. As a result, the outer member 12 is substantially hourglass-shaped as a whole. The degree of constriction of the outer member 12 can be appropriately determined. In order to obtain a clean appearance as in the forms illustrated in FIGS. 1 to 6, the narrowest portion is preferably narrower than the width of the inner member 200, but the narrowest portion may be determined to be equal to or greater than the width of the inner member 200.

As illustrated in FIGS. 3 to 5, the outer member 12 has a first sheet layer 12S adjacent to the outside of the elastic member 19 and a second sheet layer 12H adjacent to the inside of the elastic member 19. The material of the first sheet layer 12S and the second sheet layer 12H is not particularly limited, but a nonwoven fabric can be suitably used. As the nonwoven fabric, a raw fiber thereof is not particularly limited. Examples of the raw fiber include synthetic fibers formed of polyolefin such as polyethylene and polypropylene, polyester, and polyamide, regenerated fibers such as rayon and cupra, natural fibers such as cotton, mixed fibers in which two or more of these are used, and composite fibers. Further, the nonwoven fabric may be manufactured by any manufacturing method. When flexibility is emphasized, as at least one of the first sheet layer 12S and the second sheet layer 12H, a nonwoven fabric of polypropylene (PP) or a copolymer (for example, a copolymer in which ethylene is used as a copolymerization component) (hereinafter referred to as "PP type nonwoven fabric"), or a nonwoven fabric of a sheath/core fiber (PE/PP) with polyethylene (PE) as a sheath and polypropylene (PP) as a core component is preferably used. Examples of the processing method include known methods such as a spun lace method, a spunbond method, a thermal bond method, a melt blown method, a needle punch method, an air-through method, and a point bond method. In particular, from the viewpoints of excellent strength and flexibility, a spunbond nonwoven fabric is preferable, more particularly, a spunbond nonwoven fabric formed by laminating a plurality of spunbond layers, for example, SS nonwoven fabric (two layers) or SSS nonwoven fabric (three layers) can be suitably used, and four or more layers spunbond nonwoven fabric can also be used. The thickness and basis weight of the nonwoven fabric are not particularly limited, but it is desirable that the thickness is 0.1 to 1 mm, and the basis weight is about 10 to 20 g/m$^2$.

The first sheet layer 12S and the second sheet layer 12H may be one layer and the other sheet layer which are stacked by folding back one sheet material, also may be a layer composed of separate sheet materials, or may be both of them. Further, at least one of the first sheet layer 12S and the second sheet layer 12H may be partially formed of a sheet material different from that of other portions. The outer member 12 of the illustrated form has a first sheet material and a second sheet material. The first sheet material has an external surface side portion extending from an edge of the waist opening WO of the front body to an edge of the waist opening of the back body and a folded-back portion 12r folded back inward at the edge of the waist opening WO of the front body (extending so as to cover an end portion on the waist opening WO side of the inner member 200). The second sheet material is joined to the inside of the external surface side portion of the first sheet. Although the first sheet material and the second sheet material respectively form the first sheet layer 12S and the second sheet layer 12H, the present invention is not limited thereto. For example, although not illustrated, in the waist portion W, the external surface side portion and the folded-back portion 12r of the first sheet material may form the first sheet layer 12S and the second sheet layer 12H respectively, and in the lower waist portion U and the intermediate portion L, the first sheet material and the second sheet material may form the first sheet layer 12S and the second sheet layer 12H, respectively.

To enhance the fitness to the body, the outer member 12 has a continuous stretchable region 23, a non-stretchable region 21, and an intermittent stretchable region 22. The continuous stretchable region 23 continuously extends in the width direction in the area nearer to the waist opening WO than the absorber 56. The non-stretchable region 21 is provided in the middle in the width direction in the front-back direction range having the absorber 56. The intermittent stretchable region 22 is provided on both sides in the width direction of the non-stretchable region 21. Between the first sheet layer 12S and the second sheet layer 12H in the continuous stretchable region 23 and the intermittent stretchable region 22, elongated elastic members 19 (15 to 17) such as rubber thread are attached at a predetermined stretch rate along the width direction to be stretchable in the width direction (the width direction is a stretching direction). As the elastic member 19, synthetic rubber may be used, and also natural rubber may be used. The continuous stretchable region 23 may be formed over the entire width direction in a part or the whole of the front-back direction range having the non-stretchable region 21 and the intermittent stretchable region 22 in the illustrated form. Alternatively, the front-back direction range of the non-stretchable region 21 in the illustrated form may be expanded on the waist side or the crotch side.

To be more specific about the illustrated form, the waist portion W of the outer member 12 is formed as the continuous stretchable region 23, and between the first sheet layer 12S and the second sheet layer 12H, a plurality of the waist portion elastic members 17 are attached with intervals in the front-back direction in a stretched state along the width direction at a predetermined stretch rate so as to continuously extend over the whole of the width direction. One or a plurality of the waist portion elastic members 17 disposed adjacent to the lower waist portion U may overlap with the absorber 56. A portion adjacent to the lower waist portion U in the waist portion W may be a region having the non-stretchable region 21 and the intermittent stretchable region 22 similarly to the lower waist portion U. As the waist portion elastic members 17, about 3 to 22 rubber threads each having a fineness of 155 to 1880 dtex, particularly about 470 to 1240 dtex (in the case of synthetic rubber) (in the case of natural rubber, a cross-sectional area of about 0.05 to 1.5 mm$^2$, particularly about 0.1 to 1.0 mm$^2$) are preferably attached with intervals of 5 to 20 mm, particularly 8 to 16 mm, at a stretch rate of 150 to 400%, particularly about 220 to 320%. Further, it is not necessary to make the waist portion elastic members 17 entirely have the same fineness and stretch rate. For example, the fineness and the stretch rate of the elastic member at the upper portion of the waist portion W may be different from those of the elastic member at the lower portion of the waist portion W.

In addition, a plurality of the lower waist portion elastic members 15 each formed of an elongated elastic member is attached with intervals in the front-back direction in a stretched state along the width direction at a predetermined stretch rate so as to continuously extend over the entire width direction in each site on the upper side and both sides in the width direction, except for the non-stretchable region 21, between the first sheet layer 12S and the second sheet layer 12H of the lower waist portion U of the outer member 12. As the lower waist portion elastic member 15, about 5 to 30 rubber threads each having a fineness of 155 to 1880 dtex, particularly about 470 to 1240 dtex (in the case of synthetic rubber) (in the case of natural rubber, a cross-sectional area of about 0.05 to 1.5 mm$^2$, particularly about 0.1 to 1.0 mm$^2$) are preferably attached with intervals of 5 to 20 mm, particularly 8 to 16 mm, at a stretch rate of 200 to 350%, particularly about 240 to 300%.

Further, a plurality of the intermediate elastic members 16, each formed of an elongated elastic member are attached with intervals in the front-back direction in a stretched state along the width direction at a predetermined stretch rate so as to continuously extend over the entire width direction in each portion on the both sides in the width direction, except for the non-stretchable region 21, between the first sheet layer 12S and the second sheet layer 12H of the intermediate portion L of the outer member 12. As the elastic members of the intermediate portion 16, about 2 to 10 rubber threads having a fineness of 155 to 1880 dtex, particularly about 470 to 1240 dtex (in the case of synthetic rubber) (in the case of natural rubber, a cross-sectional area of about 0.05 to 1.5 mm$^2$, particularly about 0.1 to 1.0 mm$^2$) are preferably attached with intervals of 5 to 20 mm, particularly 8 to 16 mm, at a stretch rate of 150 to 300%, particularly 180 to 260%.

As with the intermittent stretchable region 22 in the illustrated form, in the case where the elastic member 19 (the lower waist portion elastic member 15 and the elastic member of the intermediate portion 16 in the illustrated form) provided in the outer member 12 is arranged on both sides in the width direction, except for the non-stretchable region 21, shrinkage of the absorber 56 in the width direction is prevented in the non-stretchable region 21. Therefore, it is preferable that the non-stretchable region 21 is the intermediate region in the width direction (preferably including the entire joint region 201 between the inner member 200 and the outer member 12) including a part of or the whole of a portion overlapping in the width direction with the absorber 56, and the entire region in the width direction to the side seal portion 12A on both sides in the width direction is the intermittent stretchable region 22.

(Divided Structure of Outer Member)

Figure 7:
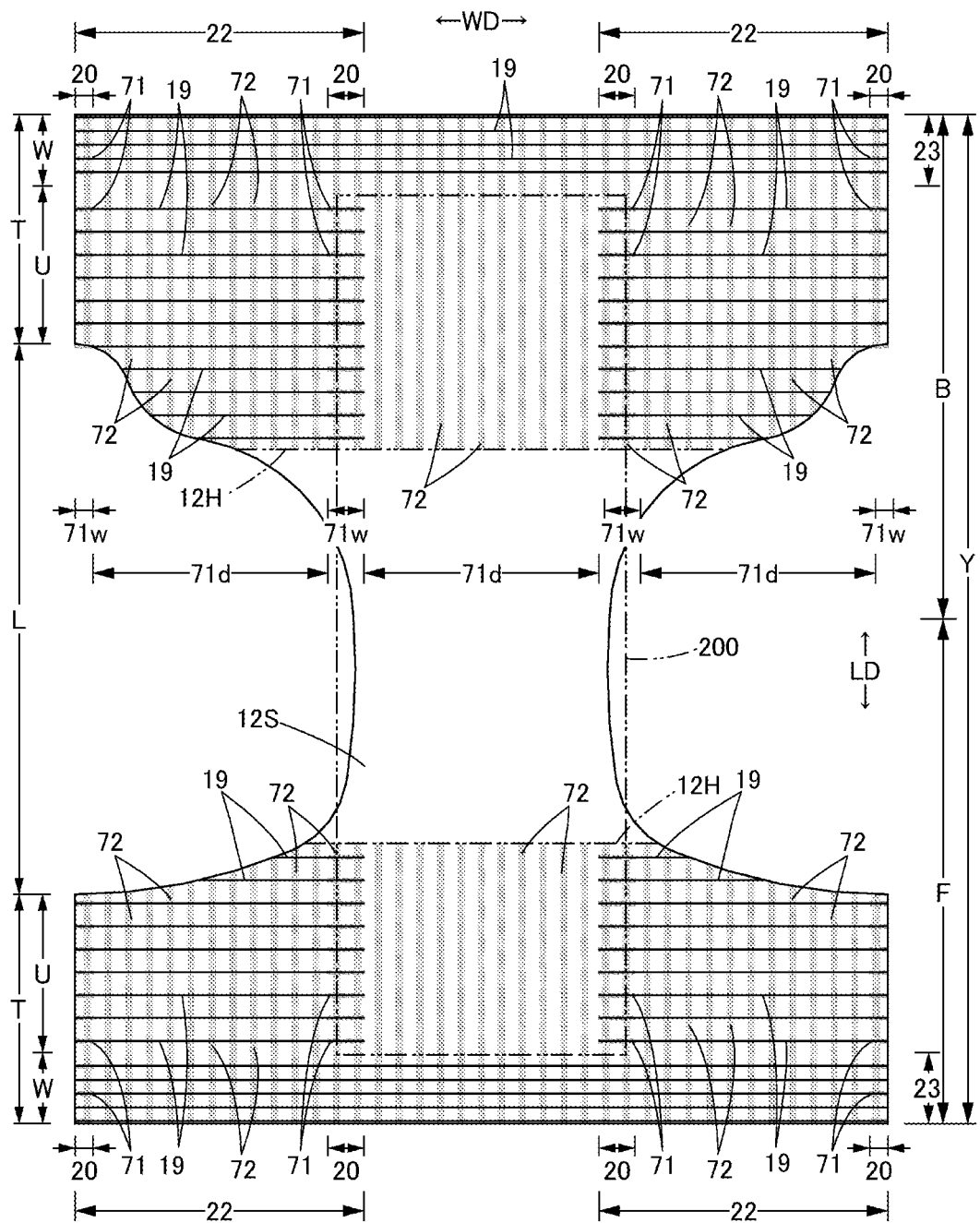
FIG. 7 is a plan view illustrating an outer member in a spread state.
Figure 8:
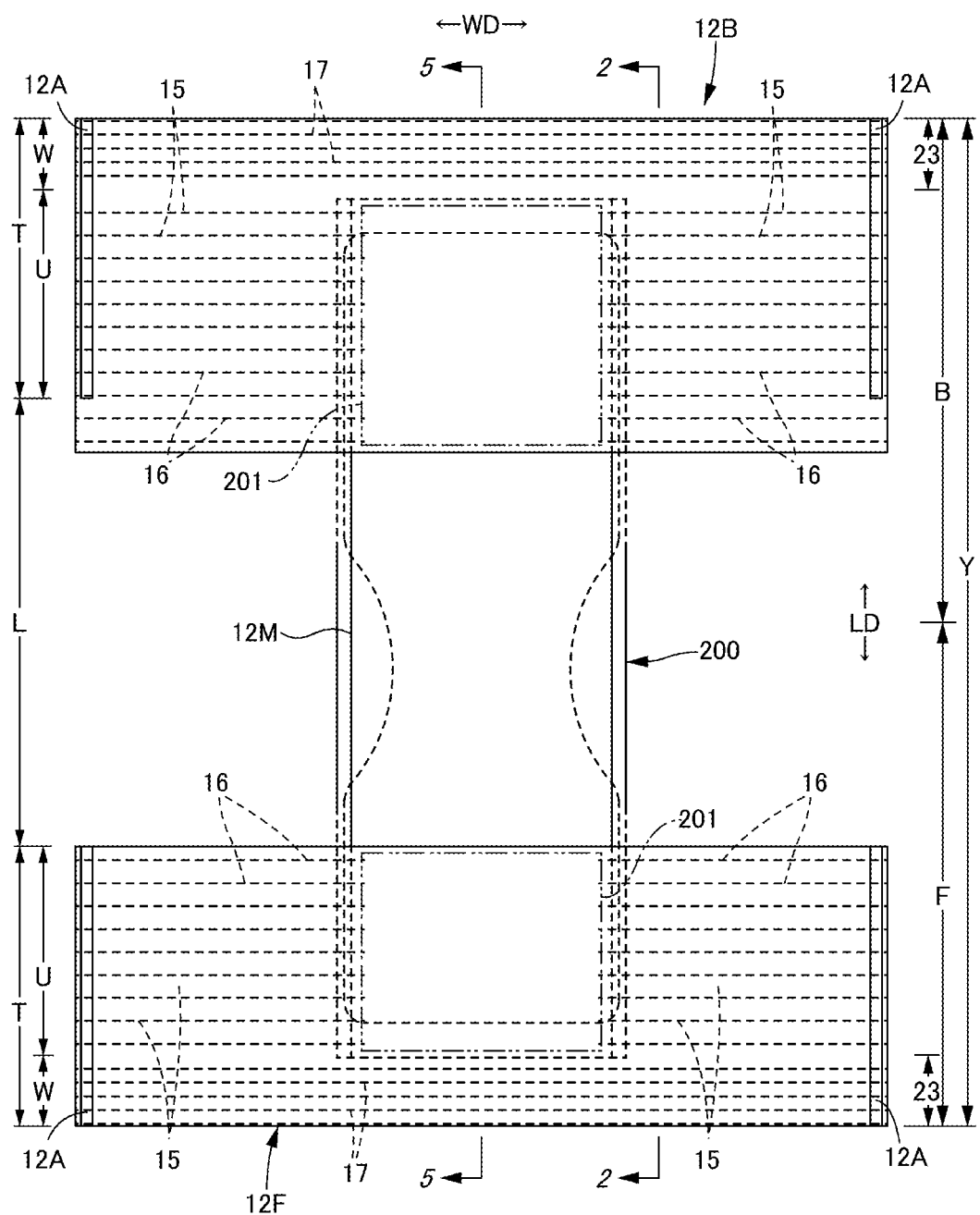
FIG. 8 is a plan view illustrating the outer surface of an underpants-type disposable diaper in a state where a diaper is spread.
Figure 9:
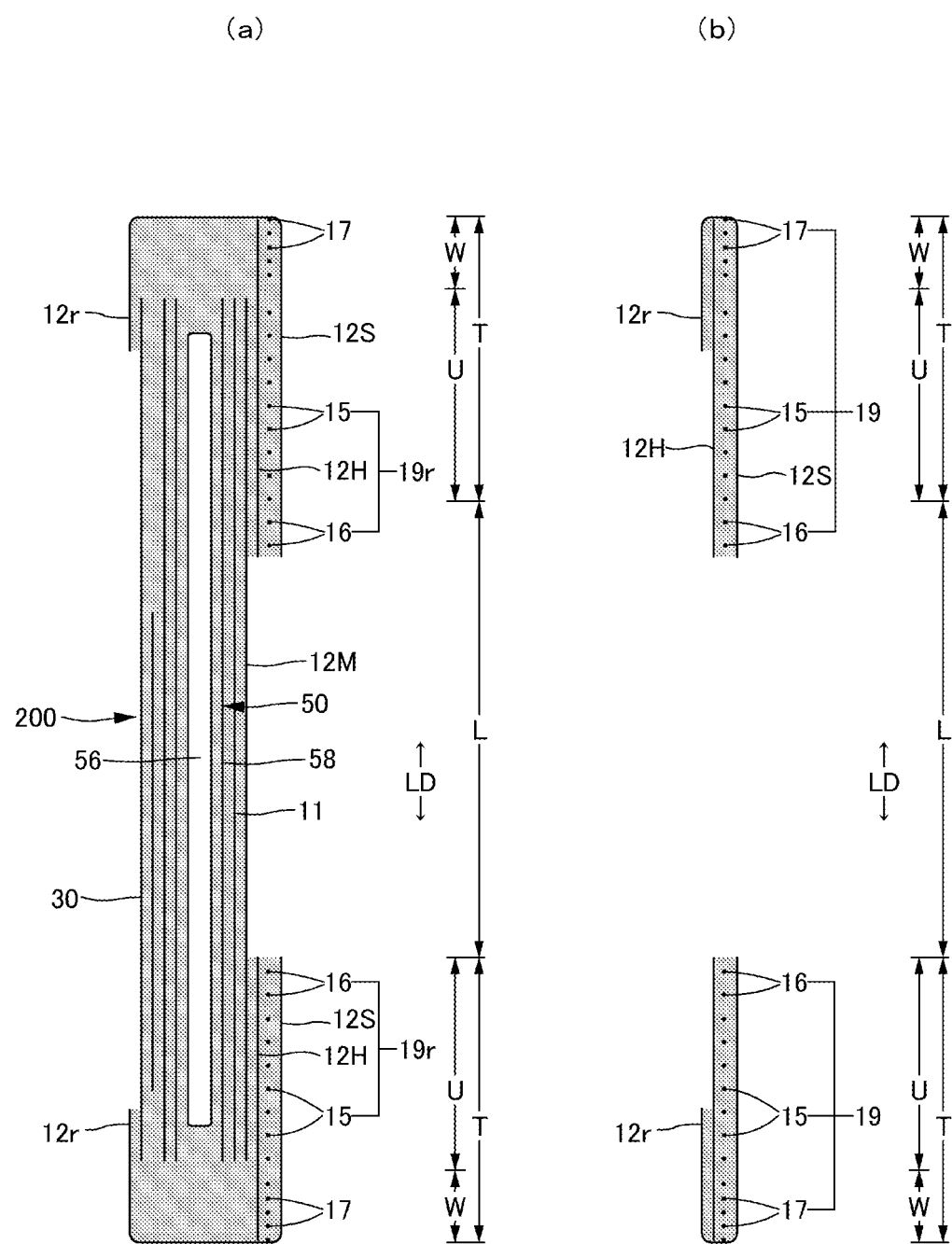
FIG. 9(a) is a cross-sectional view taken along line 5-5 in FIG. 8.
FIG. 9(b) is a cross-sectional view taken along line 2-2 in FIG. 8.
Figure 10:
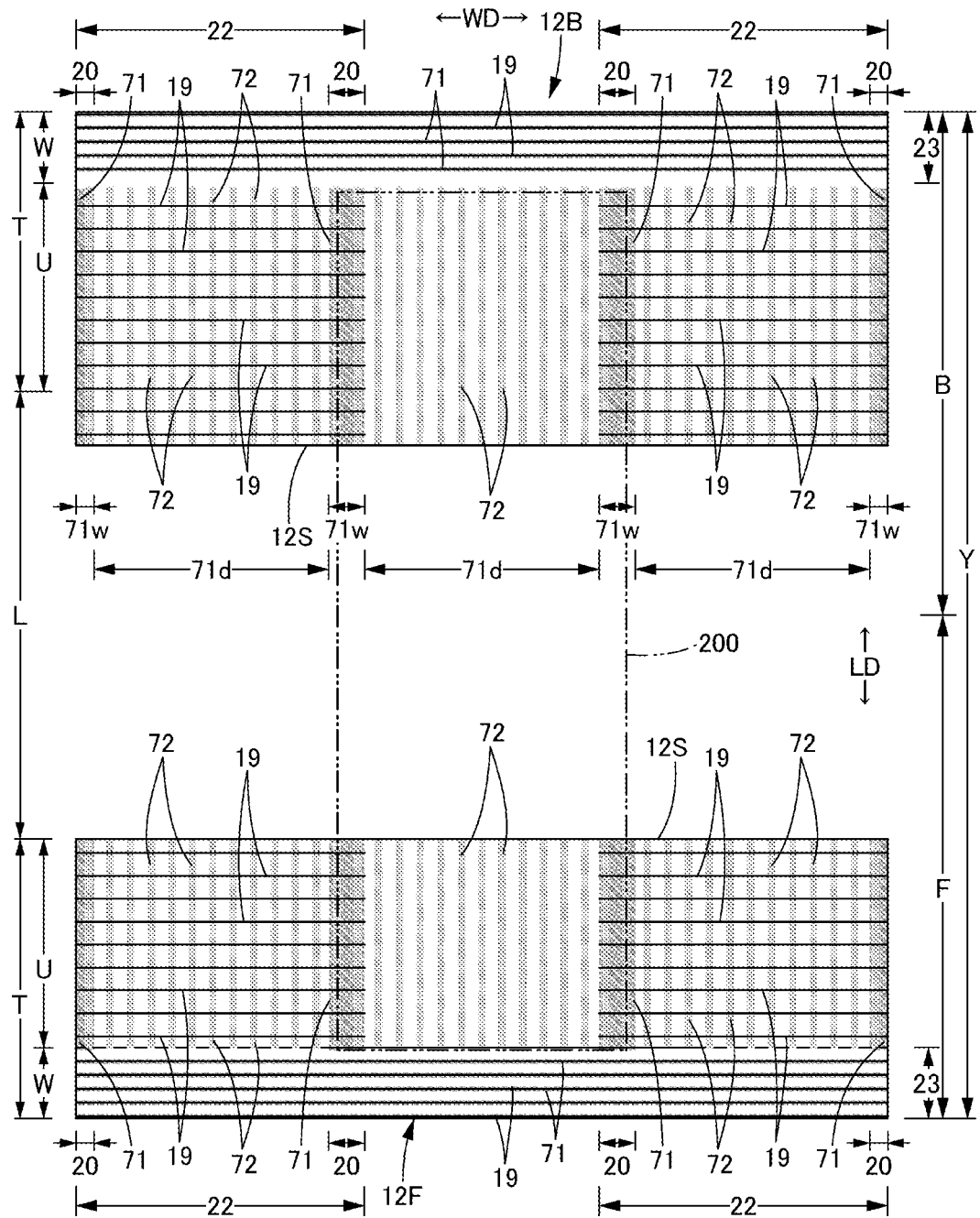
FIG. 10 is a plan view illustrating an outer member in a spread state.

In the examples illustrated in FIGS. 1 to 7, the front body F to the back body B are continuously covered by the integral outer member 12, but as in the examples illustrated in FIGS. 8 to 10, the outer members 12F and 12B may be composed of a front outer member 12F which is a part constituting the front body F and a back outer member 12B which is a part constituting the back body B. The front outer member 12F and the back outer member 12B are not continuous on the crotch side and may be separated in the front-back direction LD. This separation distance 12d can be set to about 150 to 250 mm. It is desirable to bond a crotch portion cover sheet 12M so as to cover a part (for example, a range which is extending over the entire portion exposed between the front outer member 12F and the back outer member 12B in the front-back direction, but not extending to the front/back ends of the inner member 200, and in which both side edges in the width direction WD do not reach both side edges of the inner member 200) or the entire exposed portion of the back surface of the inner member 200 in this separation portion. However, it can be omitted. As the crotch portion cover sheet 12M, the same materials as those that used for the first sheet layer and the second sheet layer can be used.

(About Stretchable Structure)

In this underpants-type disposable diaper, as illustrated in FIGS. 2 to 7 and FIGS. 8 to 10, a plurality of elongated elastic members 19 are provided at intervals along the with direction (stretching direction) in a region from the waist portion W to the intermediate portion L, between the first sheet layer 12S and the second sheet layer 12H. The underpants-type disposable diaper is provided with an adhesive region of the first hot melt adhesive 71 for fixing the elastic member 19 to at least one of the first sheet layer 12S and the second sheet layer 12H at the end portion 20 in the width direction of the stretchable regions 22 and 23, and an adhesive region of the second hot melt adhesive 72 for adhering the first sheet layer 12S and the second sheet layer 12H in a region other than the adhesive region of the first hot melt adhesive 71.

(Adhesion of Elastic Member)

More specifically, both end portions 20 in the width direction of the continuous stretchable region 23 are both end portions in the width direction of a product, and the waist portion elastic members 17 are fixed to at least one of the first sheet layer 12S and the second sheet layer 12H in an adhesive region of the first hot melt adhesive 71 positioned at both end portions in the width direction of the product. On the other hand, one side of the both end portions 20 in the width direction of the intermittent stretchable region 22 is positioned at the end portion 20 in the width direction of a product, and the other side is the end portion 20 adjacent to the non-stretchable region. The lower waist portion elastic members 15 are fixed to at least one of the first sheet layer 12S and the second sheet layer 12H in an adhesive region of the first hot melt adhesive 71 positioned at the end portion 20, and the intermediate elastic members 16 are fixed to at least one of the first sheet layer 12S and the second sheet layer 12H in an adhesive region of the first hot melt adhesive 71 positioned at the end portion adjacent to the non-stretchable region.

In this embodiment, since both sides in the width direction of the intermediate portion L are cut along the leg periphery, only the lower waist portion U is a stretchable structure of the present invention, but at the time of manufacture, it is possible to integrally form the stretchable structure extending over the lower waist portion U and the intermediate portion L by the forming method to be described later. That is, in the lower waist portion U, the intervals 71d of the adhesive regions of the first hot melt adhesive 71 adjacent in the width direction are all the same at three positions, and twice of the width direction length 71w of the adhesive region of the first hot melt adhesive 71 positioned at both end portions in the width direction of a product and the width direction length 71w of the adhesive region of the first hot melt adhesive 71 positioned at the end of the stretchable region 22 on the side of the non-stretchable region 21 are the same at all four places. As a result, as will be described later, the application sites of the first hot melt adhesive 71 at the starting time of manufacturing equipment is not erroneously positioned, and it makes manufacturing very easy.

On the other hand, in the embodiment of the divided structure of the outer member illustrated in FIGS. 8 to 10, the waist portion elastic members 17 are fixed to at least one of the first sheet layer 12S and the second sheet layer 12H via the first hot melt adhesive 71 disposed only at a position overlapping with the waist portion elastic members 17 over the entire width direction of the waist portion elastic members 17 in the continuous stretchable region 23. Further, in the intermittent stretchable region 22, the lower waist portion elastic members 15 and the elastic member of the intermediate portion 16 are fixed to at least one of the first sheet layer 12S and the second sheet layer 12H in the adhesive region of the first hot melt adhesive 71 positioned at each of the end portion in the width direction and the end portion adjacent to the non-stretchable region of a product.

In this embodiment, the stretchable structure of the entire intermittent stretchable region 22 (the lower waist portion U and the intermediate part L) is the stretchable structure of the present invention, and this stretchable structure can be integrally formed by the forming method to be described later. That is, in the intermittent stretchable region 22, the intervals 71d of the adhesive regions of the first hot melt adhesive 71 adjacent in the width direction are all the same at three places, and twice of the width direction length 71w of the adhesive region of the first hot melt adhesive 71 positioned at both end portions in the width direction of a product and the width direction length 71w of the adhesive region of the first hot melt adhesive 71 positioned at the end portion of the stretchable region 22 on the side of the non-stretchable region 21 are the same at all four places. Therefore, also in this embodiment, as will be described later, the application site of the first hot melt adhesive 71 at the starting time of manufacturing equipment is not erroneously positioned, and it makes manufacturing very easy.

Figure 11:
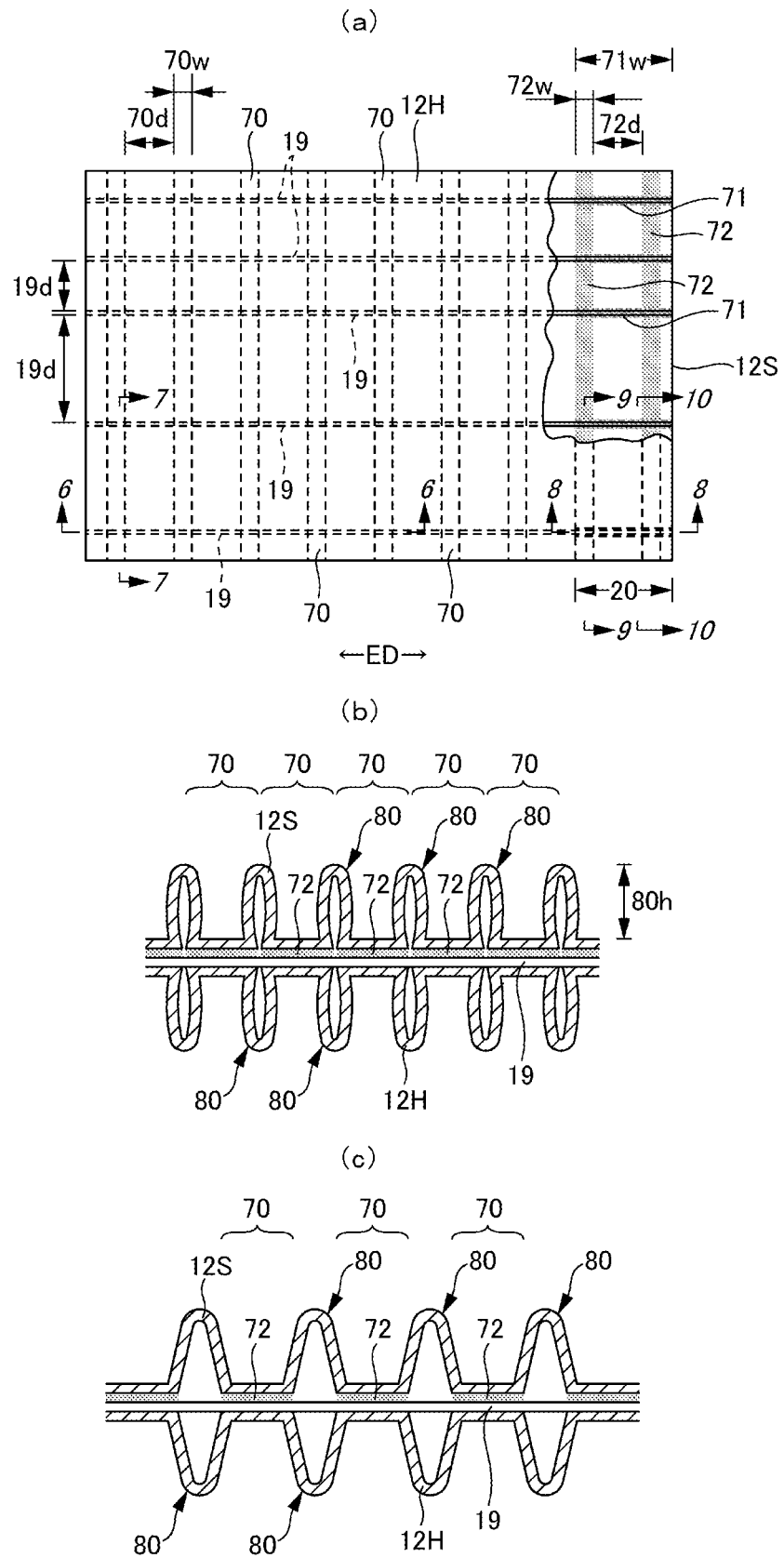
FIG. 11(a) is a plan view of a stretchable structure in a spread state.
FIG. 11(b) is a cross-sectional view taken along line 6-6 in a natural length state.
FIG. 11(c) is a cross-sectional view taken along line 6-6 in a state extending to some extent.
Figure 13:
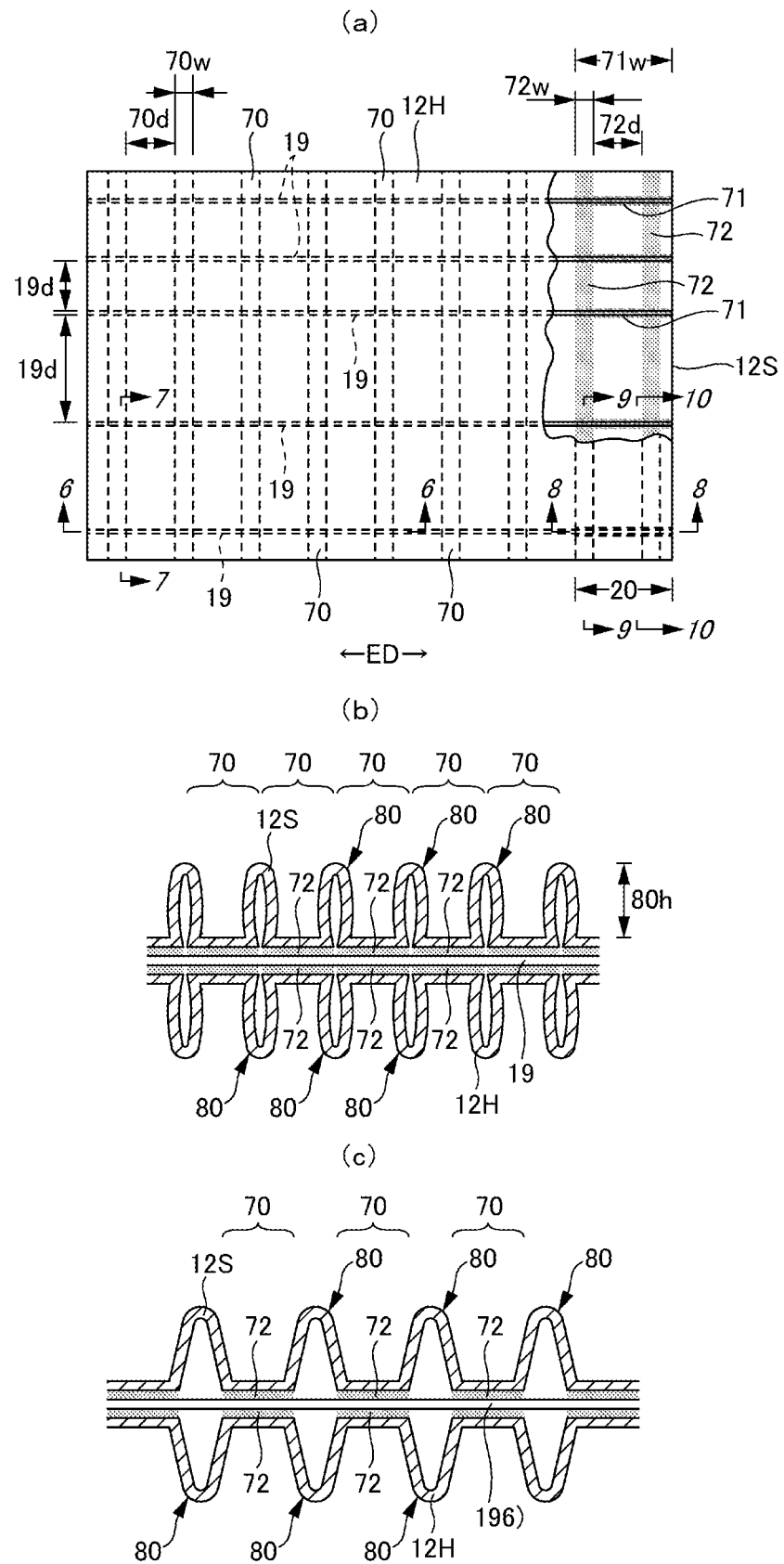
FIG. 13(a) is a plan view of a stretchable structure in a spread state.
FIG. 13(b) is a cross-sectional view taken along line 6-6 in a natural length state.
FIG. 13(c) is a cross-sectional view taken along line 6-6 in a state stretching to some extent.
Figure 15:
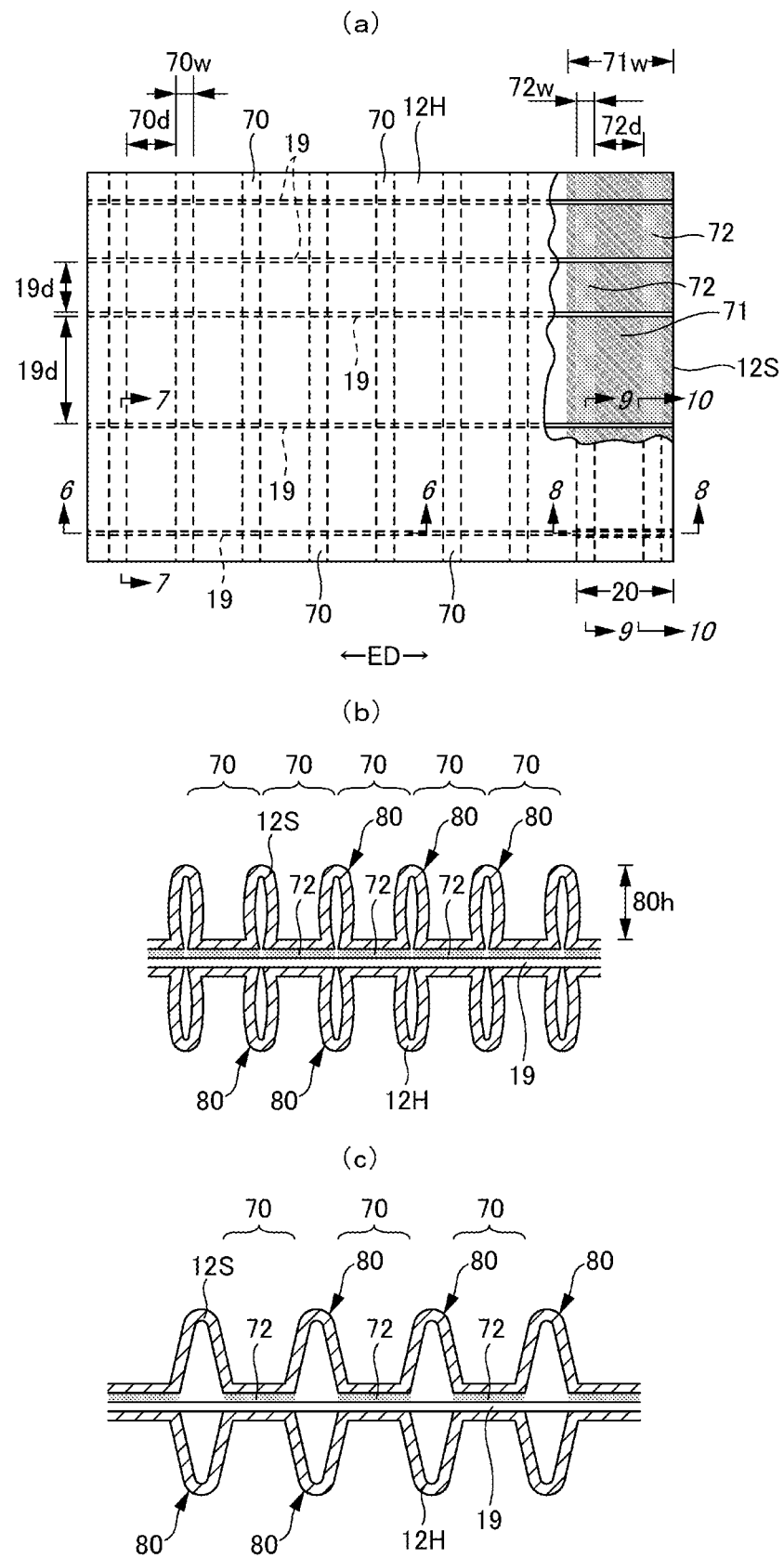
FIG. 15(a) is a plan view of a stretchable structure in a spread state.
FIG. 15(b) is a cross-sectional view taken along line 6-6 in a natural length state.
FIG. 15(c) is a cross-sectional view taken along line 6-6 in a state stretching to some extent.

As illustrated in FIGS. 7, 11 and 13, the first hot melt adhesive 71 is disposed intermittently in a direction orthogonal to the elastic member 19 and at a position overlapping with the elastic member 19. Further, as illustrated in FIGS. 10 and 15, the hot melt adhesive 71 can be disposed in a pattern continuing in the front-back direction so as to extend over the end portions of a plurality of the elastic members 19. In the former case, it is preferable that the first hot melt adhesive 71 is applied only to the outer peripheral surface of the elastic member 19 by an application means such as a comb gun or a sure wrap nozzle. In the latter case, it is preferable that the first hot melt adhesive 71 is applied to at least one of the first sheet layer 12S and the second sheet layer 12H by slot coating, curtain coating, or the like.

Incidentally, regarding the adhesive region of the first hot melt adhesive 71, the interval 71d in the adhesive regions adjacent in the width direction, the width direction length 71w of the adhesive region positioned at both ends in the width direction of a product, and the width direction length 71w of the adhesive region positioned at the end portion of the stretchable region on the non-stretchable region side may be determined appropriately. In the usual case, it is preferable that the interval 71d between the adhesive regions adjacent in the width direction is about 45 to 95% of the width direction length of the stretchable region 22, and a specific length is preferably 65 to 130 mm. In addition, the width direction length 71w of the adhesive region positioned at the end portion of the stretchable region 22 on the side of the non-stretchable region 21 is preferably about 5 to 35% of the MD direction length of the stretchable region 22, and a specific length is preferably 8 to 50 mm. The width direction length 71w of the adhesive region positioned at both ends in the width direction of a product is ½ of the width direction length 71w of the adhesive region positioned at the end portion of the stretchable region 22 on the side of the non-stretchable region 21.

(Bonding of the First Sheet Layer and the Second Sheet Layer)

The second hot melt adhesive 72 for bonding the first sheet layer 12S and the second sheet layer 12H may be disposed in any range and in any pattern as long as the first sheet layer 12S and the second sheet layer 12H are bonded at portions other than the fixing portion of the elastic member 19 at the end portions of the stretchable regions 22 and 23. However, it is preferable that the second hot melt adhesive 72 is provided in a uniform pattern over the whole region of the stretchable structure including the end portions of the non-stretchable region 21 and the stretchable regions 22 and 23 as in the illustrated form.

For example, although not illustrated, the second hot melt adhesive 72 is applied to the outer peripheral surface of the elastic member 19 by an application means such as a comb gun or a sure wrap nozzle, and the second hot melt adhesive 72 may be disposed intermittently in a direction orthogonal to the elastic member 19 and only at a position overlapping with the elastic member 19. Although not illustrated, the second hot melt adhesive 72 may be disposed at least intermittently in the front-back direction or intermittently in the front-back direction and the width direction so as not to overlap with the elastic members 19.

As illustrated in FIGS. 7, 10, and 11 to 16, the sheet bonded portion 70 in which the first sheet layer 12S and the second sheet layer 12H are bonded via the second hot melt adhesive 72 is disposed intermittently in the longitudinal direction of the elastic members 19 and in a striped patter which is continuous in a direction intersecting with the elastic members 19. This cross-direction continuous bonded form is one preferable form to since it forms clean continuous pleats 80. In this embodiment, the elastic members 19 are fixed to at least one of the first sheet layer 12S and the second sheet layer 12H via at least the first hot melt adhesive 71 at both ends in the width direction of the stretchable regions 22 and 23 and are to at least one of the first sheet layer 12S and the second sheet layer 12H at a position intersecting with the sheet bonded portion 70 via the second hot melt adhesive 72.

In this cross-direction continuous bonded form, along with the contraction of the elastic members 19, as each illustrated in FIGS. 11(b), 13(b), and 15(b), the portions positioned between the sheet joint portions 70 in the first sheet layer 12S and the second sheet layer 12H contract and protrude in the opposite direction from each other to form the pleats 80. FIGS. 11(b), 13(b), and 15(b) indicate a state of natural length. The elastic members 19 are extended from this state to some extent at the time of wearing, and as illustrated in FIGS. 11(c), 13(c), and 15(c), the hem of the pleat 80 spreads. As a result, the height 80h of the pleat 80 decreases. In addition, since this stretchable structure is in the cross-direction continuous bonded form, the pleats 80 extending straightly are formed along the sheet bonded portion 70, and air permeability and appearance are excellent.

Figure 12:
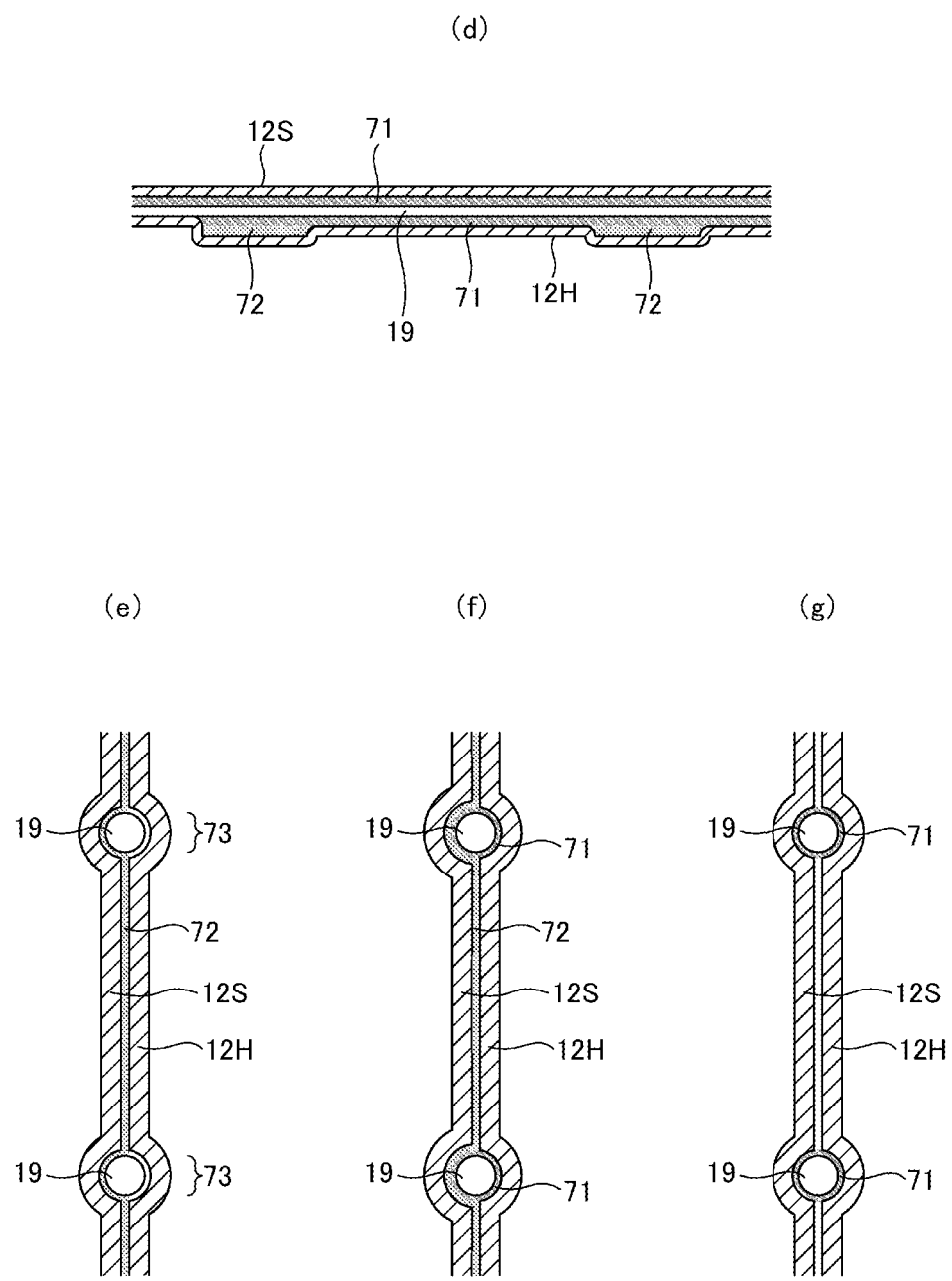
FIG. 12(d) is a cross-sectional view taken along line 8-8 in FIG. 11.
FIG. 12(e) is a cross-sectional view taken along line 7-7 in FIG. 11.
FIG. 12(f) is a cross-sectional view taken along line 9-9 in FIG. 11.
FIG. 12(g) is a cross-sectional view taken along line 10-10 in FIG. 11.

In the embodiment illustrated in FIGS. 11 and 12, on the surface of the first sheet layer 12S on the second sheet layer 12H side, the second hot melt adhesive 72 is applied intermittently in the stretching direction and continuously in a predetermined width in a direction intersecting with the stretching direction. On the surface of the second sheet layer 12H on the first sheet layer 12S side, the second hot melt adhesive 72 is not applied, the elastic members 19 are sandwiched between the first sheet layer 12S and the second sheet layer 12H in a stretched state, and each of the first sheet layer 12S and the second sheet layer 12H, and the first sheet layer 12S and the elastic members 19 are joined by the second hot melt adhesive 72. In this case, among the portions where the sheet bonded portion 70 and the elastic members 19 intersect, since the second hot melt adhesive 72 is continuous in the direction intersecting with the stretching direction on the side of the first sheet layer 12S of the elastic members 19, the elastic members 19 are fixed to the first sheet layer 12S via the second hot melt adhesive 72. On the side of the second sheet layer 12H of the elastic members 19, the second hot melt adhesive 72 becomes discontinuous in the direction intersecting with the stretching direction. In FIG. 12(e), this discontinuous portion is denoted by reference sign 73. Since the second hot melt adhesive 72 intermittently exists in the second sheet layer 12H, a decrease in flexibility of the second sheet layer 12H, and a decrease in the flexibility as a whole of the first sheet layer 12S and the second sheet layer 12H can be suppressed. Further, at the portion where the elastic members 19 intersect with the sheet bonded portion 70, although the second hot melt adhesive 72 continuously extends only on the side of the first sheet layer 12S, on the both sides of elastic members 19, the first sheet layer 12S and the second sheet layer 12H are integrated by the sheet bonded portion 70. Therefore, the contraction force of the elastic members 19 acts on the first sheet layer 12S and the second sheet layer 12H in substantially the same manner, and uniform pleats can be formed on both the first sheet layer 12S and the second sheet layer 12H.

Figure 14:
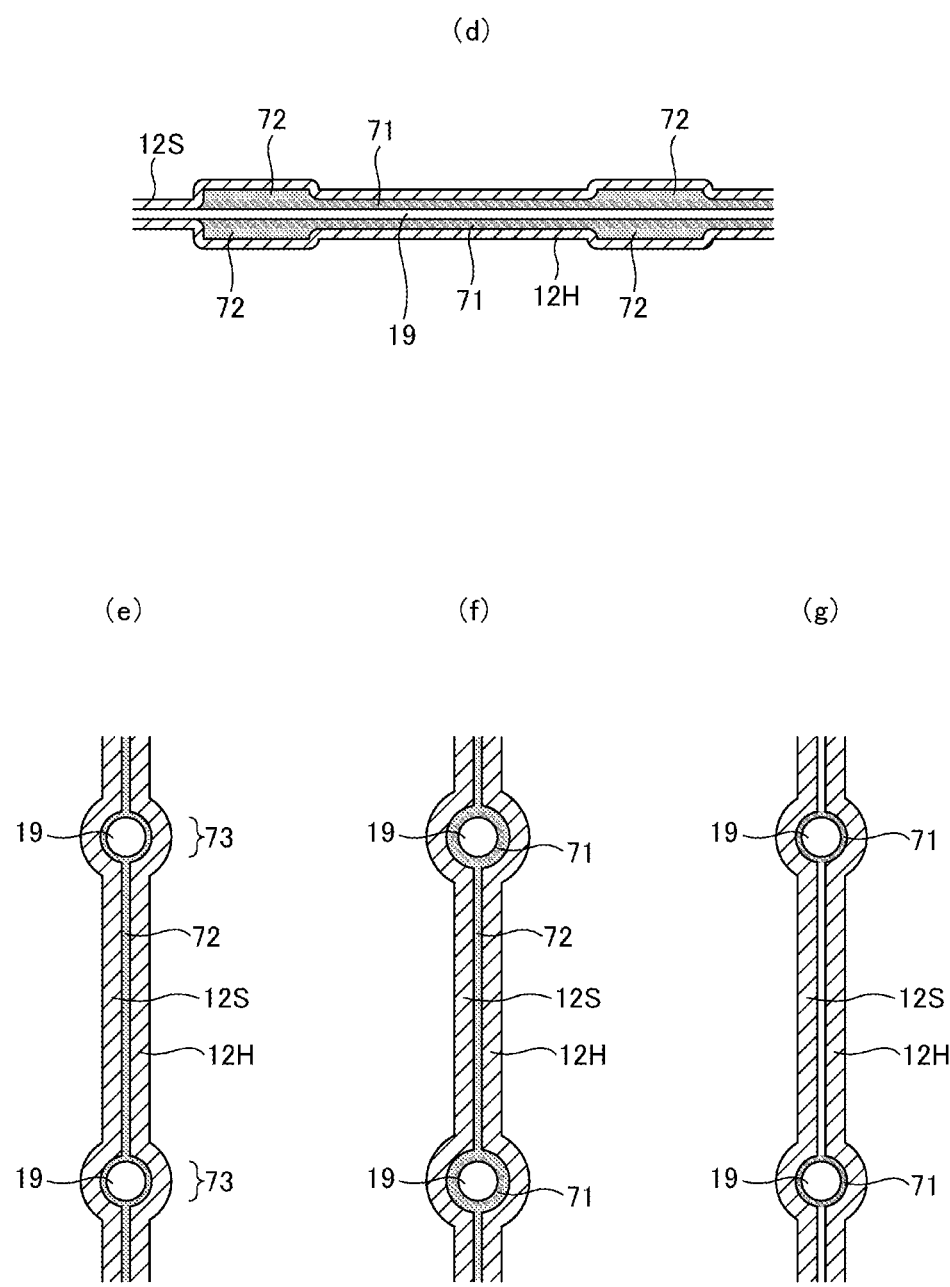
FIG. 14(d) is a cross-sectional view taken along line 8-8 in FIG. 13.
FIG. 14(e) is a cross-sectional view taken along line 7-7 in FIG. 13.
FIG. 14(f) is a cross-sectional view taken along line 9-9 in FIG. 13.
FIG. 14(g) is a cross-sectional view taken along line 10-10 in FIG. 13.

It is also possible to apply the adhesive 71 to the first sheet layer 12S and the second sheet layer 12H with the same pattern. In this case, as illustrated in FIGS. 13 and 14, since the second hot melt adhesive 72 is continuous in a predetermined width in a direction intersecting with the stretching direction on both the first sheet layer 12S side and the second sheet layer 12H side of the elastic members 19 among the portions where the sheet bonded portion 70 intersects with the elastic members 19, there is an advantage that the elastic members 19 can be more firmly fixed. Although not illustrated, the elastic members 19 can be fixed by sandwiching them between the second sheet layer 12H and the first sheet layer 12S while applying the second hot melt adhesive 72 to the second sheet layer 12H and not applying the second hot melt adhesive 72 to the first sheet layer 12S. However, in these embodiments, since the second hot melt adhesive 72 is continuous on the second sheet layer 12H, the flexibility of the second sheet layer 12H itself to be brought into contact with the skin is deteriorated, and the portion where flexibility is reduced is pressed against the skin by the elastic members 19. Therefore, it is not preferable. Accordingly, it is desirable that the second hot melt adhesive 72 is not continuous on the side having the surface that contacts the skin of a wearer like the second sheet layer 12H as in the embodiments indicated in FIGS. 11 and 12.

In such embodiments, the width 70w of each sheet bonded portion 70 in the stretching direction is preferably set to 0.5 to 4 mm (particularly 0.5 to 1 mm), and the interval 70d between the adjacent sheet bonded portions 70 is preferably set to 4 to 8 mm (particularly, 5 to 7 mm). Basically, if the width 70w of the bonded portion 70 in the stretching direction is too narrow, application of the second hot melt adhesive 72 becomes difficult, whereas if the width 70w is too wide, the flexibility reduces. Furthermore, the width 70w in the stretching direction of each sheet bonded portion 70 affects the interval between adjacent pleats 80. If the width of the pleat 80 to be formed is thin, and the width is thicker than 4 mm as in the cross-direction continuous bonded form, the space between adjacent pleats 80 becomes too wide, and individual pleats 80 have independent appearance. In addition, when the pleats 80 causes deformation such as collapse, spreading, and falls due to a compressive force in the thickness direction, the force of supporting the adjacent pleats 80 weakens. As a result, resistance to the deformation and restoration after the deformation also weaken, and fullness becomes insufficient.

In addition, by merely setting the width 70w of the sheet bonded portion 70 in the stretching direction to 0.5 to 4 mm, when the interval 70d between adjacent sheet bonded portions 70 is less than 4 mm or more than 8 mm, the following can be said. That is, the interval 70d between adjacent sheet bonded portions 70 affects the height 80h and width of the pleats 80, and if the interval between adjacent sheet bonded portions is about 2 mm, the pleats 80 have poor continuity in the longitudinal direction as with the case of continuously fixing in the stretching direction (there is no meaning to provide the sheet bonded portions 70 intermittently in the stretching portion). If the interval is 3 mm, the pleats 80 straightly extend in the direction orthogonal to the stretching direction, but the effects of supporting the adjacent pleats 80 each other cannot be expected, and fullness becomes insufficient. In addition, when the interval 70d between the sheet bonded portions 70 exceeds 8 mm, the pleats 80 are crushed irregularly due to the compression during packaging, and the product appearance deteriorates. On the other hand, when the width 70w of the sheet joint portions 70 in the stretching direction is 0.5 to 4 mm, and the interval 70d between the sheet bonded portions 70 is 4 to 8 mm, sufficient fullness can be obtained for the first time, and the pleats 80 are hardly collapsed irregularly by the compression at the time of packaging.

It is desirable that the width 70w of the sheet bonded portion 70 is narrow for increasing the flexibility, for example, 1 mm or less. However, it is inevitable that the fixing force of the elastic members 19 by the second hot melt adhesive 72 is reduced, and thus it is very important to fix the elastic members 19 at the end portions of the stretchable regions 22 and 23 via the first hot melt adhesive 71 having higher holding power as described above.

The interval 19d between the elastic members 19 adjacent to each other can be appropriately determined. However, when the interval exceeds 10 mm, although not as large as the longitudinal intermittent bonding form, the thickness of the pleats 80 changes in a direction intersecting with the stretching direction and the pleats 80 becomes lumpy. Therefore, in the present invention, it is preferable that the interval 19d between the adjacent elastic members 19 is 10 mm or less, particularly 3 to 7 mm.

The shape of the sheet bonded portion 70 (the second hot melt adhesive 72) can be appropriately determined and may be a wave shape or a shape extending in an oblique direction with respect to the elastic members 19, but the shape linearly extending in a direction orthogonal to the elastic members 19 is preferable.

Instead of the second hot melt adhesive 72, the first sheet layer 12S and the second sheet layer 12H can be directly welded by heat sealing or ultrasonic sealing. In this case, a hot melt adhesive is not applied between the first sheet layer 12S and the second sheet layer 12H in regions other than the adhesive region of the first hot melt adhesive 71 disposed at the end portions of the stretchable regions 22 and 23.

(Hot Melt Adhesive)

Examples of the first hot melt adhesive 71 and the second hot melt adhesive 72 include, but are not limited to, adhesives of the EVA type, adhesive rubber type (elastomer type), polyolefin, polyester, and polyamide. As the first hot melt adhesive 71 and the second hot melt adhesive 72, the same types can be used, but it is preferable that the holding power of the first hot melt adhesive 71 is higher than the holding power of the second hot melt adhesive 72. In particular, the holding power of the first hot melt adhesive 71 is preferably greater than 120 minutes, and the holding power of the second hot melt adhesive 72 is preferably 30 to 90 minutes. In this way, if the holding power of the first hot melt adhesive 71 is higher than the holding power of the second hot melt adhesive 72, the elastic members 19 are more firmly fixed at the end portions of the stretchable regions 22 and 23, and the first sheet layer 12S and the second sheet layer 12H can be bonded more flexibly in regions other than the end portions of the stretchable regions 22 and 23. In this case, the portion where the elastic members 19 at the end portions of the stretchable regions 22 and 23 is fixed by the first hot melt adhesive 71 has a harder touch, but the influence is local. Since the elastic members 19 are firmly fixed at the end portions of the stretchable regions 22 and 23, it is not necessary for the second hot melt adhesive 72 in the other region to carry almost the function of fixing the elastic members 19, and since it suffices to bond the first sheet layer 12S and the second sheet layer 12H, even lower holding forces will have no problem and rather provide the advantage that the main stretchable region becomes further flexible.

In addition, since the hot melt adhesive having a high melt viscosity generally has a high holding power, it is desirable that the melt viscosity of the first hot melt adhesive 71 is higher than the melt viscosity of the second hot melt adhesive 72. To be more specific, the first hot melt adhesive 71 preferably has a melt viscosity of 10,000 to 40,000 mPa·s at a temperature of 140° C. and a melt viscosity of 5,000 to 10,000 mPa·s at a temperature of 160° C., and the second hot melt adhesive 72 preferably has a melt viscosity of 3,000 to 7,000 mPa·s at a temperature of 140° C. and a melt viscosity of 1,000 to 4,000 mPa·s at a temperature of 160° C.

Further, since the hot melt adhesive having high loop tack adhesion is suitable for bonding nonwoven fabrics to each other, it is desirable that the loop tack adhesion of the second hot melt adhesive 72 is higher than the loop tack adhesion of the first hot melt adhesive 71. Specifically, the loop tack adhesion of the first hot melt adhesive 71 is preferably 10 to 500 g/25 mm, and the loop tack adhesion of the second hot melt adhesive 72 is preferably 1,000 g/25 mm or more.

It is more preferable that the peeling strength of the first hot melt adhesive 71 is 100 cN/25 mm or more in both length and width, and the peeling strength of the second hot melt adhesive 72 is 100 cN/25 mm or more in both length and width.

The first hot melt adhesive 71 and the second hot melt adhesive 72 that satisfy such requirements can be easily obtained from a hot melt adhesive manufacturer.

Although the basis weight (coating amount) of the first hot melt adhesive 71 and the second hot melt adhesive 72 can be appropriately determined, it is preferable that the basis weight is in the range of 3 to 30 g/m², in particular in the range of 10 to 20 g/m².

(Positional Relationship Between First Hot Melt Adhesive and Second Hot Melt Adhesive)

Figure 16:
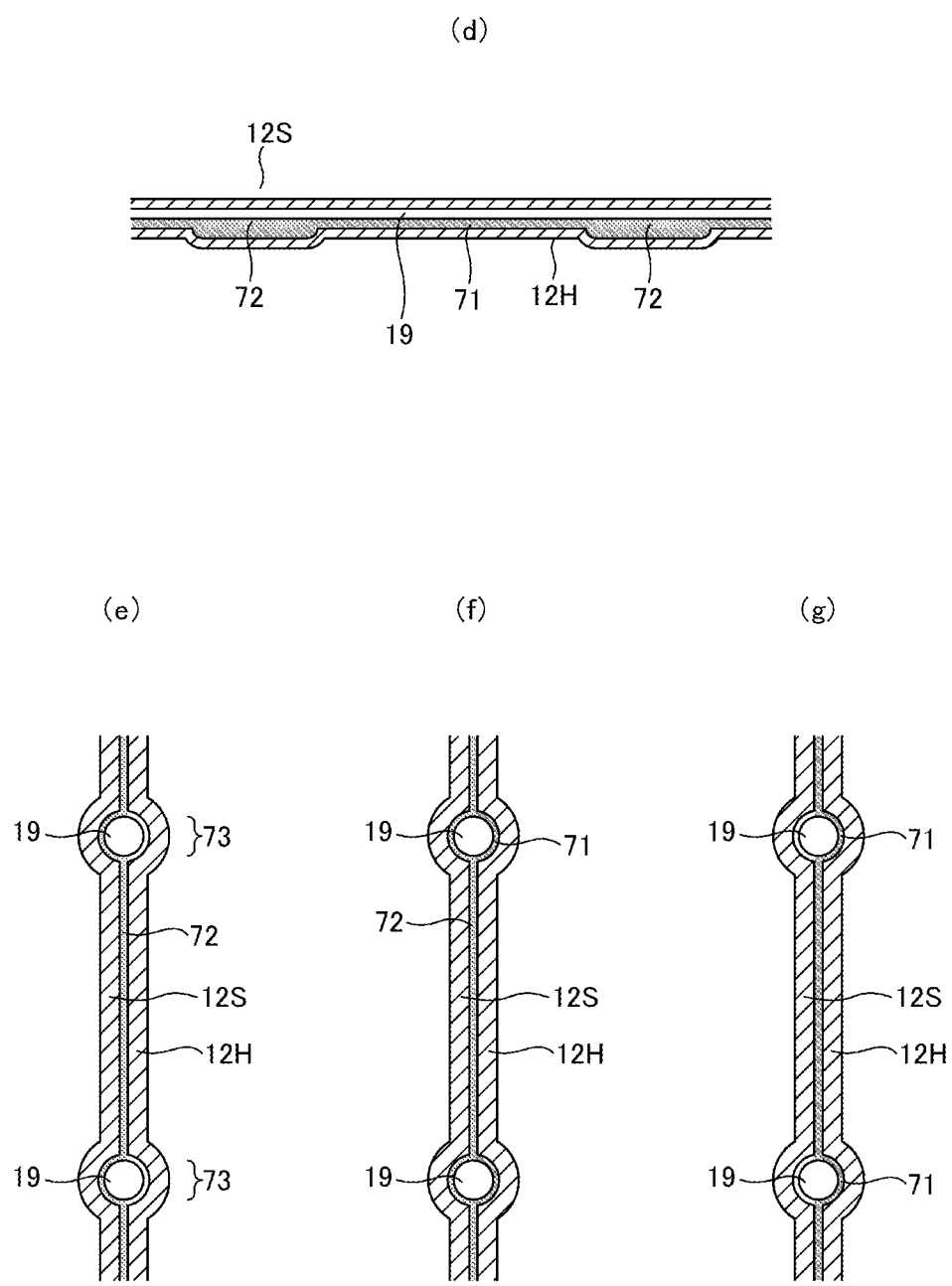
FIG. 16(d) is a cross-sectional view taken along line 8-8 in FIG. 15.
FIG. 16(e) is a cross-sectional view taken along line 7-7 in FIG. 15.
FIG. 16(f) is a cross-sectional view taken along line 9-9 in FIG. 15.
FIG. 16(g) is a cross-sectional view taken along line 10-10 in FIG. 15.

As illustrated in FIGS. 12, 14, and 16, in at least a part of each adhesive region using the first hot melt adhesive 71, the elastic members 19 are preferably bonded to at least one of the first sheet layer 12S and the second sheet layer 12H without using the second hot melt adhesive 72. Even when the holding power of the first hot melt adhesive 71 is higher than that of the second hot melt adhesive 72, in the case where the layer of the first hot melt adhesive 71 and the layer of the second hot melt adhesive 72 are interposed (in the case of double coating) between adherent targets, as compared with the case where only the layer of the second hot melt adhesive 72 is interposed, the fixing force of the elastic member 19 is high, but cohesive failure of the layer is likely to occur by the interposition of the layer of the second hot melt adhesive 72, and the fixing force of the elastic member 19 is lowered.

Therefore, it is conceivable (not illustrated) that the first hot melt adhesive 71 and the second hot melt adhesive 72 are arranged so as not to overlap each other at the position where the elastic member 19 passes. However, when the positions of the first hot melt adhesive 71 and the second hot melt adhesive 72 are different as described above, it is necessary to intermittently apply the first hot melt adhesive 71 and the second hot melt adhesive 72, and accurate position control of the first hot melt adhesive 71 and the second hot melt adhesive 72 is considerably difficult.

Accordingly, as illustrated in FIGS. 7 and 10 and FIGS. 11 to 16, as a preferable embodiment, the second hot melt adhesive 72 is arranged (double coating) at portions including the end portions of the stretchable regions 22 and 23 with an intermittent pattern at least in the stretching direction, and the first hot melt adhesive 71 is continuously applied at the end portions of the stretchable regions 22 and 23 in the stretching direction longer than the width of each second hot melt adhesive 72. As a result, in the arrangement portion of the first hot melt adhesive 71, although a double portion where the first hot melt adhesive 71 and the second hot melt adhesive 72 overlap is partially formed, also a single portion of the first hot melt adhesive 71 is certainly formed between the second hot melt adhesives 72. Therefore, the elastic members 19 can be bonded via only the first hot melt adhesive 71. In this case, the continuous width 71w of the first hot melt adhesive 71 may be appropriately determined, but it is preferably five times or more of the width 72w of the second hot melt adhesive 72. Further, it is preferably 1.5 times or more, particularly 2 times of more, of the interval 72d in the stretching direction of the adjacent second hot melt adhesive 72. In a usual case, it is preferable that the total width of the portion where the first hot melt adhesive 71 adheres the elastic members 19 without using the second hot melt adhesive 72 is about 5 to 30 mm. As a preferable intermittent pattern of the second hot melt adhesive 72, a cross-direction continuous joining form to be described later can be exemplified.

<Method of Forming Stretchable Structure>

Figure 17:
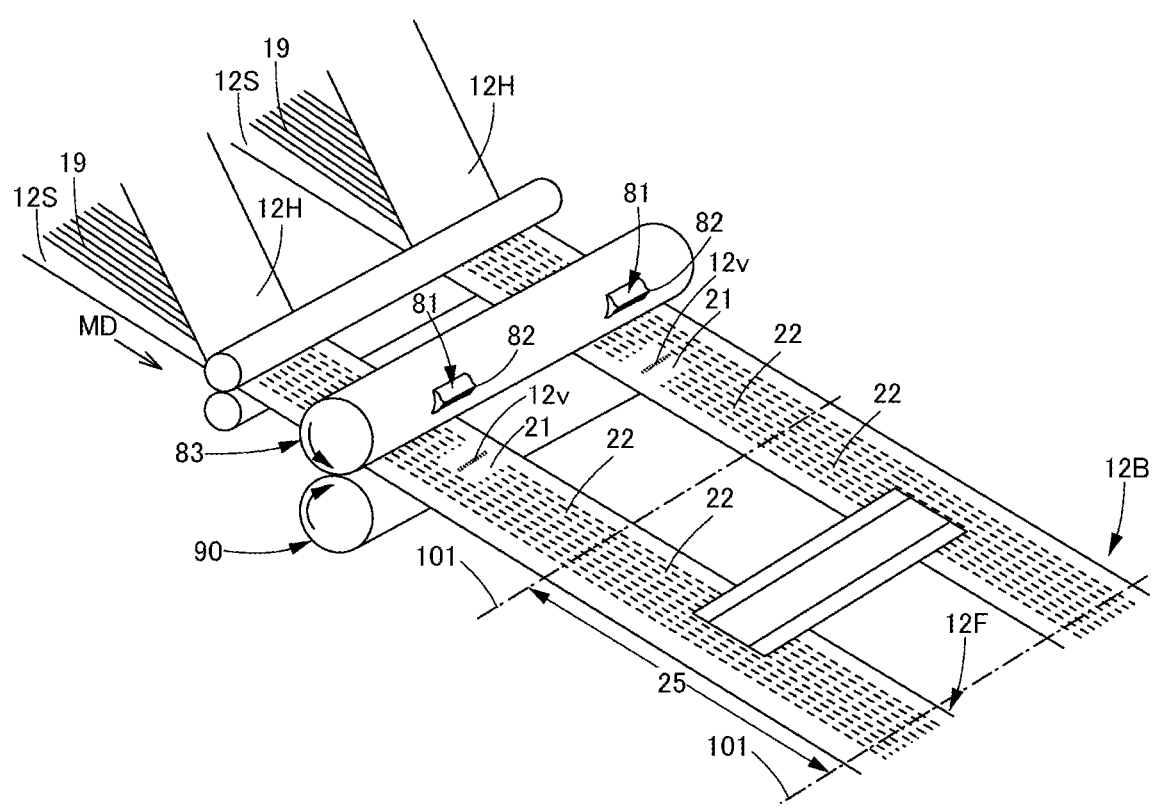
FIG. 17 is a perspective view of a main part of a manufacturing flow of an underpants-type disposable diaper.

FIG. 17 shows a main part of an assembling process in manufacturing of an underpants-type disposable diaper. That is, while continuously conveying the first sheet layer 12S and the second sheet layer 12H in the MD, the elastic members 19 are continuously sandwiched between the first sheet layer 12S and the second sheet layer 12H in the MD, and the elastic member 19 is fixed to one of the first sheet layer 12S and the second sheet layer 12H. After that, a unit stretchable structure 25, in which the stretchable region 22 and the non-stretchable region 21 obtained by cutting the elastic members 19 are alternately repeated three or more regions in the MD, and both ends in the MD become the stretchable regions 22, is repeatedly formed in the MD. Then, although not illustrated, after folding so as to match the front body on one side in the cross direction (CD) and the back body on the other side in the CD, a side seal portion 12A is formed, and cutting is performed at a boundary 101 of a part to be an individual product. Note that the flow illustrated in FIG. 17 is based on the assumption of manufacturing of an underpants-type disposable diaper of outer two-piece type similar to that illustrate in FIG. 10.

Figure 18:
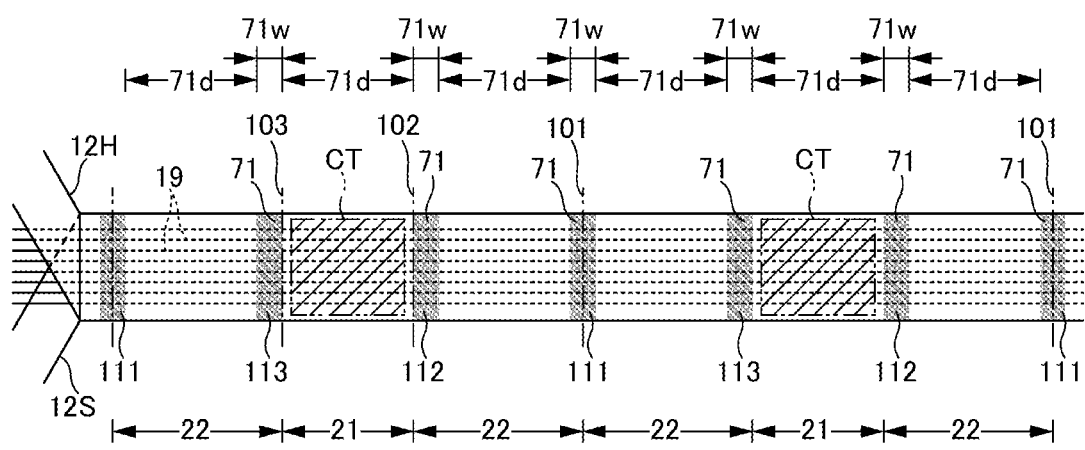
FIG. 18 is a plan view of an example of a coating pattern of a first hot-melt adhesive.

In fixing the elastic member 19, as illustrated in FIG. 18, the elastic members 19 are fixed to at least one of the first sheet layer 12S and the second sheet layer 12H via the first hot melt adhesive 71 in the application regions 111 to 113 of the first hot melt adhesive 71 disposed in each of a portion to be the end portion 20 of the stretchable region of a pair of unit stretchable structures adjacent in the MD, and a portion to be the end portion on the non-stretchable region 21 side of the stretchable regions 22 and 23. The first hot melt adhesive 71 may be applied to the elastic members 19 or to at least one of the first sheet layer 12S and the second sheet layer 12H. In FIG. 18, the illustration of the second hot melt adhesive 72 is omitted for the sake of clarity.

As described above, when the second hot melt adhesive is used to bond the first sheet layer and the second sheet layer, the first hot melt adhesive 71 is applied to the elastic members 19, or at least one of the first sheet layer 12S and the second sheet layer 12H, the second hot melt adhesive 72 is applied to at least one of the first sheet layer 12S and the second sheet layer 12H, and the elastic members 19 are sandwiched between both the sheet layers 12S and 12H at the same time when both the sheet layers 12S and 12H are bonded. In this case, the application method of the second hot melt adhesive 72 is not particularly limited. However, when the width 70w of the sheet bonded portion 70 in the stretching direction is narrow, for example, 1 mm or less, the application width of the second hot melt adhesive 72 becomes narrow, and the intermittent application by the application method of spraying from a nozzle, such as curtain coating or solid coating, becomes difficult. Therefore, it is desirable that a pattern coating suitable for narrow width application (transfer of the second hot melt adhesive 72 in a letterpress method) is used.

Figure 19:
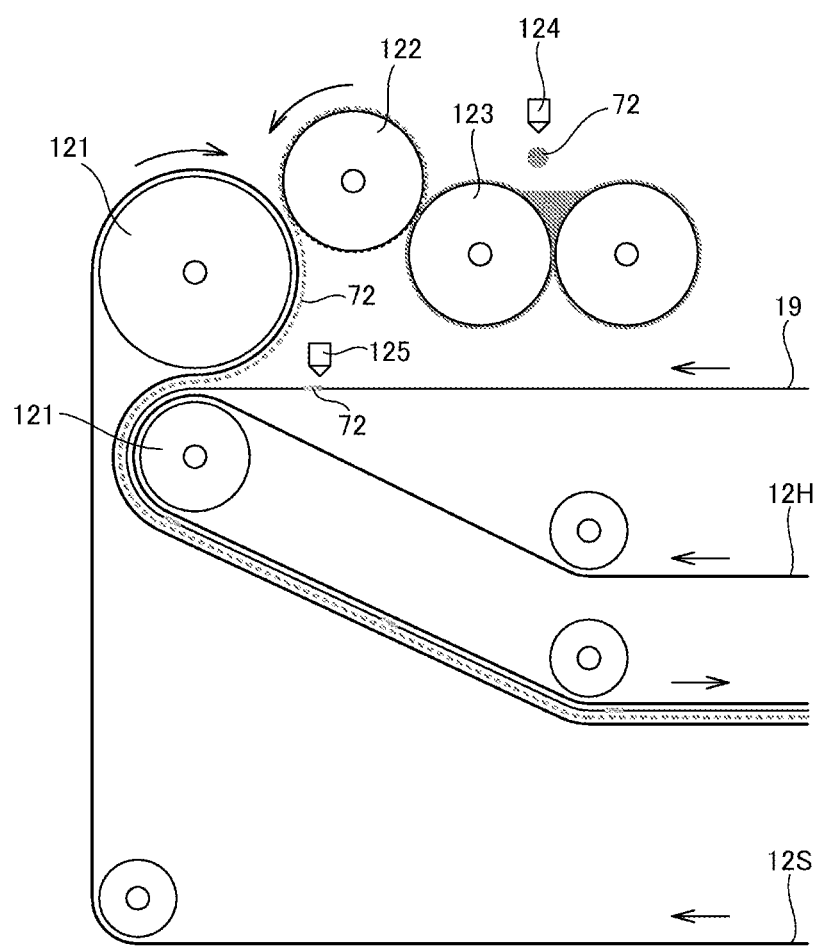
FIG. 19 is a front view of a main part of a manufacturing flow of the stretchable structure.

FIG. 19 indicates an example of a manufacturing flow using a pattern coating for applying the second hot melt adhesive 72. That is, in an equipment example of this pattern coating type, the elastic members 19 are interposed between the second sheet layer 12H and the first sheet layer 12S coated with the second hot melt adhesive 72 on the surface of the second sheet layer 12H side, and these members are fed into between a pair of nip rolls 121, and pressed to form the stretchable structure illustrated in FIGS. 11 and 12. Before being fed into the nip roll 121, the first sheet layer 12S is brought into contact with a plate roll 122 having a convex pattern corresponding to the above-described sheet bonded portion 70, that is a striped convex pattern intermittent on the outer peripheral surface in the circumferential direction (conveying direction, machine direction: MD, a direction being the stretching direction) and continuous in the axial direction (direction intersecting with the conveying direction, cross direction: CD), and the second hot melt adhesive 72 held on the convex pattern of the plate roll 122 is transferred and applied. The reference sign 123 denotes a hot melt adhesive supply roll (anilox roll in letterpress printing) for transferring and applying the second hot melt adhesive 72 to the convex pattern of the plate roll 122 with a predetermined thickness. The reference sign 124 denotes a supply nozzle for supplying the second hot melt adhesive 72 to the hot melt adhesive supply roll 123.

In the illustrated form, the first hot melt adhesive 71 for fixing the fixed end portion of the elastic members 19 are applied intermittently in the conveying direction to the outer peripheral surface of the elastic members 19 from the nozzle 125 disposed at the conveying position in the process of conveying the elastic members 19 on the upstream side of the crimping position to dispose intermittently in a direction orthogonal to the elastic members 19 and so as to overlap with the elastic members 19. However, by an appropriate nozzle for pattern coating, spraying, curtain coating, or the like, the first hot melt adhesive 71 may be intermittently applied to at least one of the first sheet layer 12S and the second sheet layer 12H in the conveying direction.

When the unit stretchable structure is repeatedly formed in the MD, the non-stretchable region 21 is intermittently formed in the MD. After fixing the elastic members 19 to at least one of the first sheet layer 12S and the second sheet layer 12H, in a region to be the non-stretchable region 21, the non-stretchable region 21 can be formed by killing elasticity in the non-stretchable region 21 while the elasticity is left in the stretchable region 22. Killing is performed by cutting the elastic member 19 at one or more places in the middle in the width direction or cutting almost the entire elastic member 19 finely. Cutting of the elastic member 19 can be carried out by a known method without particular limitation, such as cutting by only pressurizing or cutting by heating the pressurized site while pressurizing. In the example illustrated in FIG. 17, an object to be cut is sandwiched between a sealing roll 83 provided with a pressurizing portion 81 having a cutting convex portion 82 heated to a desired temperature at one place in the circumferential direction on the outer peripheral surface and an anvil roll 90 having a smooth surface and opposed to the sealing roll 83. The object to be cut includes the elastic members 19 sandwiched between the first sheet layer 12S and the second sheet layer 12H, and the elastic members 19 are pressurized and heated to cut only a portion sandwiched between the cutting convex portion 82 and the outer peripheral surface of the anvil roll 90. Although not illustrated, in the case of cutting at a plurality of places, the sealing roll 83 having the cutting convex portion 82 at a plurality of places in the circumferential direction may be used.

Figure 20:
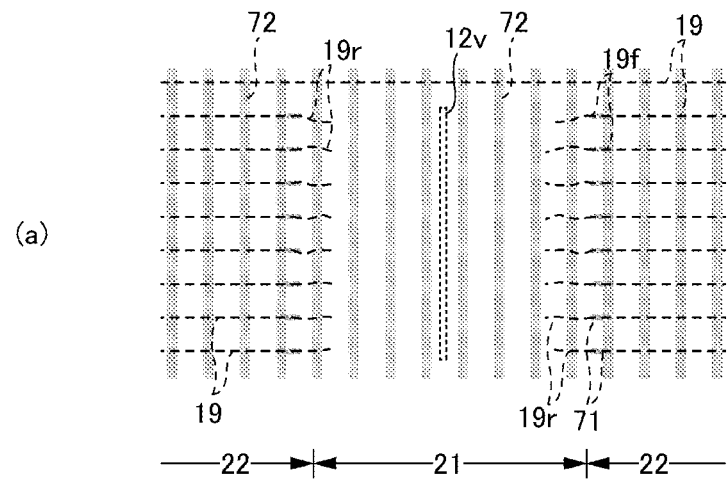
FIG. 20 is an enlarged plan view of a main part indicating various cutting aspects in a non-stretchable region.
Figure 20:
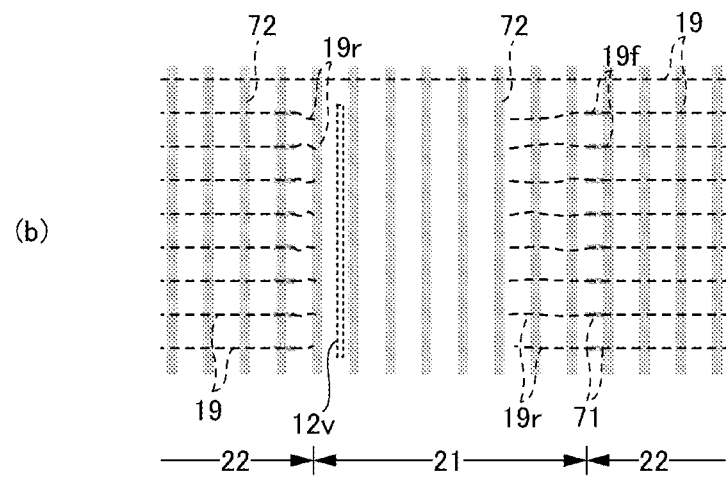
Figure 20:
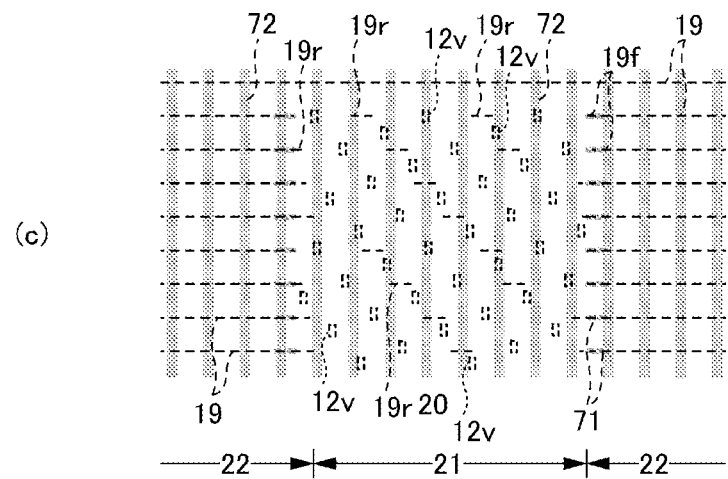
Figure 21:
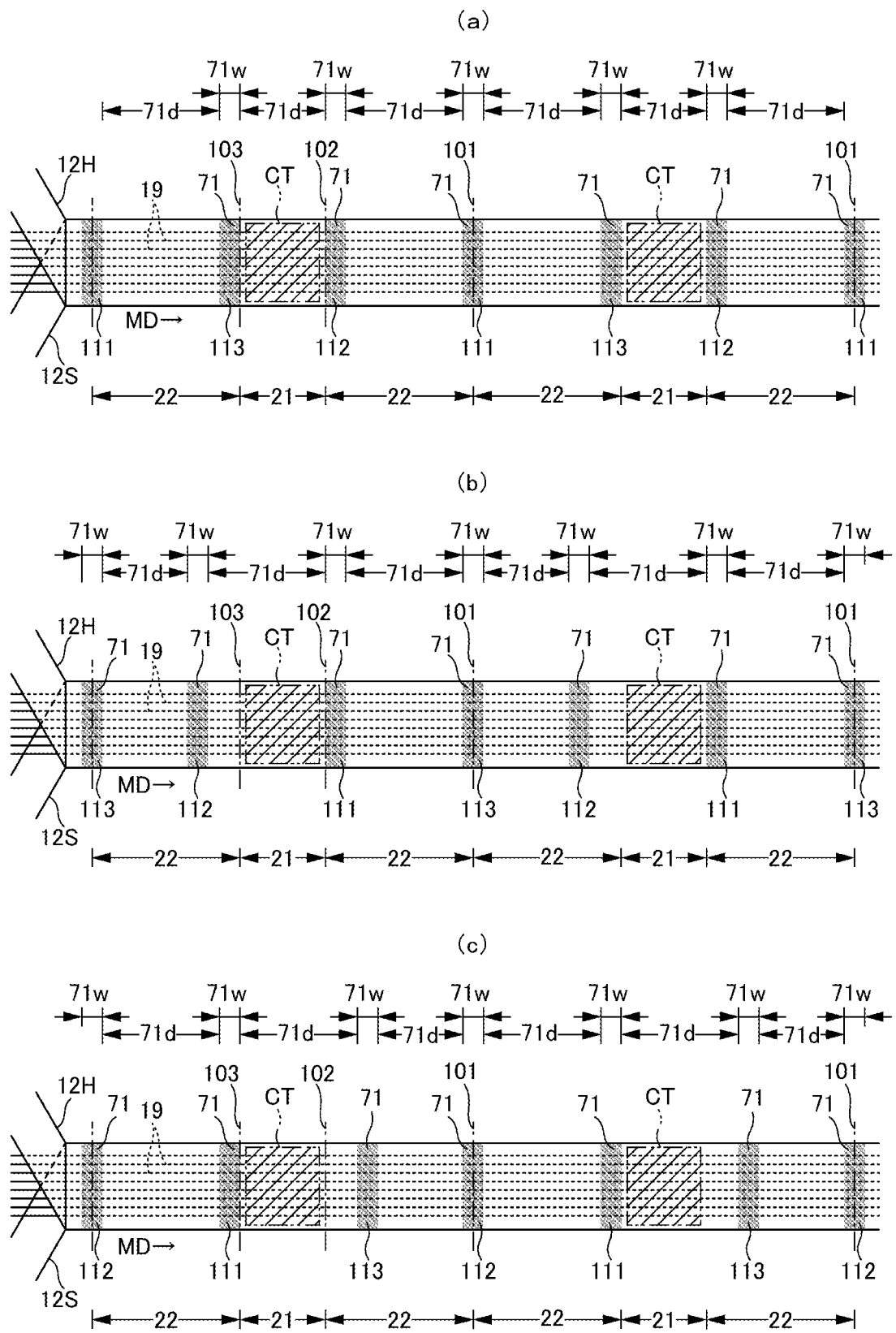
FIG. 21 is a plan view of a conventional example of a coating pattern of the first hot melt adhesive.

As a cutting pattern, for example, as illustrated in FIGS. 20(a) and 20(b), besides a pattern for cutting the elastic member at one intermediate place in the MD of the non-stretchable region 21, as illustrated in FIG. 20(c), it is possible to adopt a pattern of cutting almost the entire elastic member at many places in the MD of the non-stretchable region 21. In the former case, in products, between the first sheet layer 12S and the second sheet layer 12H in the non-stretchable region 21, only the cutting remainder continuous from the elastic member 19 in the intermittent stretchable region 22 remains as an unnecessary elastic member 19r, and only one melting trace 12v remains as a cutting trace. In the latter case, in products, between the first sheet layer 12S and the second sheet layer 12H in the non-stretchable region 21, the cutting remainder continuous from the elastic member 19 of the intermittent stretchable region 22 and the cut pieces of the elastic member discontinuous with the elastic member 19 of both of the intermittent stretchable regions 22 remain intermittently in the front-back direction and the width direction as the unnecessary elastic member 19r, and the melting trace 12v remains intermittently in the front-back direction and the width direction as cutting traces.

Although the sheet bonded portion 70 is not necessarily provided in the non-stretchable region 21, it is not preferable that the first sheet layer 12S is displaced or floated with respect to the second sheet layer 12H. Therefore, it is preferable to provide the sheet bonded portion 70 using the second hot melt adhesive 72. The sheet bonded portion 70 of the non-stretchable region 21 is not particularly limited as long as the two sheet layers 12S and 12H are adhered together. However, the sheet bonded portion 70 in the non-stretchable region 21 is preferable since, when the bonding is formed in the above-described cross-direction continuous bonding form, unnecessary elastic members 19r in the non-stretchable region 21 is fixed to the two sheet layers 12S and 12H with a hot melt adhesive.

From the viewpoints of ease of manufacturing and manufacturing stability, as illustrated in FIGS. 7 and 10, it is desirable that such the shape, size, number, and arrangement of the sheet bonded portion 70 with the second hot melt adhesive 72 in the non-stretchable region 21 are the same as those of the sheet bonded portion 70 with the second hot melt adhesive 72 in the intermittent stretchable region 22. Of course, the shape, size, number, arrangement, or the like of the sheet bonded portion 70 with the second hot melt adhesive 72 in the non-stretchable region 21 may be different from the sheet bonded portion 70 with the second hot melt adhesive 72 in the intermittent stretchable region 22.

(Application of First Hot Melt Adhesive)

Characteristically, as illustrated in FIG. 18, at the time of applying the first hot melt adhesive 71, the intervals 71$d$ of the application regions adjacent in the MD are all the same, and the MD lengths 71$w$ of all the application regions are the same. As a result, in the positioning of the application site of the first hot melt adhesive 71 at the starting time of manufacturing equipment, in principle, there is no situation in which the application region to be the starting point is erroneously set. That is, in the case of manufacturing the above-described underpants-type disposable diaper, the first hot melt adhesive 71 is applied to the first application region 111, the second application region 112, and the third application region 113 as one cycle. The first application region 111 extends over both sides in the MD of the boundary 101 of a part to be an individual product. The second application region 112 is adjacent to the stretchable region 22 side of the boundary 102 changing from the stretchable region 22 to the non-stretchable region 21. The third application region 113 is adjacent to the stretchable region 22 side of the boundary 103 changing from the non-stretchable region 21 to the stretchable region 22. At that time, if the interval 71$d$ between the application regions 111 to 113 are the same and the MD dimension 71$w$ (stretching direction dimension) are the same, it becomes unnecessary to distinguish the application regions 111 to 113 as a starting point, and it is possible to reliably apply the first hot melt adhesive 71 to a predetermined position with respect to the cutting position CT of the elastic members 19 in the non-stretchable region 21, regardless of which application regions 111 to 113 is the starting point. Therefore, the application site of the first hot melt adhesive 71 at the starting time of the manufacturing equipment is not erroneously positioned, and it makes manufacturing very easy.

Now that the interval 71$d$ between the application regions adjacent in the MD of the first hot melt adhesive and the MD direction length 71$w$ of the application region may be determined as appropriate. In the usual case, it is preferable that the interval 71$d$ between the application regions adjacent in the MD is about 45 to 95% of the MD direction length of the stretchable region 22, and a specific length is preferably 65 to 130 mm. In addition, it is preferable that the MD direction length 71$w$ in the application region is about 5 to 35% of the MD direction length of the stretchable region 22, and a specific length is preferably 8 to 50 mm <Others>

In the examples illustrated in FIGS. 7 and 10, the stretchable structure of the present invention is applied mainly to the lower waist portion U of the outer member 12 of an underpants-type disposable diaper, but the stretchable structure of the present invention can be applied to the entire front-back direction structure of the outer member 12 including the waist portion W although not illustrated. In addition, the stretchable structure of the above-described underpants-type disposable diaper has three regions in order of the stretchable region 22, the non-stretchable region 21, and the stretchable region 22 from one end to the other end, but the stretchable region 22 and the non-stretchable region 21 may repeat alternately and repeat three or more regions as long as both ends of the stretching direction become the stretchable region 22. Further, the above-described stretchable structure can also be applied to other stretchable parts such as a three-dimensional gather, a lower torso portion of a dorsal side, a leg portion, or a fastening tape of a tape type disposable diaper.

<Explanation of Terms Used Herein>

In the case where the following terms are used in the specification, those have the following meanings unless otherwise specified in the specification.

"Front-back (longitudinal) direction" means a direction connecting the ventral side (front side) and the dorsal side (back side). "Width direction" means a direction orthogonal to the front-back direction (right-left direction).

"Machine direction: MD" and "cross direction: CD" mean the flow direction (MD) in a manufacturing equipment and the lateral direction (CD) orthogonal to the flow direction, and either one is the front-back direction, and the other is the width direction. The MD of a nonwoven fabric is the direction of fiber orientation of the nonwoven fabric. "Fiber orientation" is a direction along which a fiber of a nonwoven fabric runs and determined by, for example, a measurement method in accordance with the fiber orientation test method based on the zero distance tensile strength of TAPPI standard method T481 and a simple measurement method for determining the fiber orientation direction from the tensile strength ratio of the front-back direction to the width direction.

"Spread state" means a flatly spread state without shrinkage or slackness.

"Stretch rate" means the value when the natural length is taken as 100%.

"Artificial urine" is prepared by mixing urea: 2 wt %, sodium chloride: 0.8 wt %, calcium chloride dihydrate: 0.03 wt %, magnesium sulfate heptahydrate: 0.08 wt %, and ion exchanged water: 97.09 wt %, and those are used at a temperature of 40° C. unless otherwise specified.

"Gel strength" is measured as follows: Add 1.0 g of superabsorbent polymer to 49.0 g of artificial urine and stir with a stirrer. After leaving generated gel for three hours in a thermohygrostat bath at 40° C.×60% RH, return to room temperature, and measure the gel strength with a card meter (Curdmeter-MAX ME-500, manufactured by I. techno Engineering).

"Basis weight" is measured as follows. After preliminary drying a sample or a test piece, the sample or the test piece is left in a test chamber or equipment in the standard state (the test location is at a temperature of 20±5° C. and with a relative humidity of 65% or less) to be constant weight. The preliminary drying refers to making a sample or a test piece constant weight in an environment at a temperature not exceeding 50° C. and a relative humidity of 10 to 25%. For fibers with an official moisture regain of 0.0%, preliminary drying may not be performed. A sample of dimensions of 200 mm×250 mm (±2 mm) is cut using a template for sampling (200 mm×250 mm, ±2 mm) from a test piece in a constant weight. The basis weight is set by weighing the sample, multiplying by 20, and calculating the weight per one square meter.

"Thickness" is automatically measured under the conditions of a load of 10 gf/cm$^2$ and a pressing area of 2 cm$^2$ using an automatic thickness measuring device (KES-G5 handy compression testing machine).

"Water absorption amount" is measured according to JIS K7223-1996 "Test method for water absorption of super absorbent resin".

"Water absorption rate" is the "time to end point" when JIS K7224-1996 "Test method for water absorption rate of super absorbent resin" has been carried out using 2 g of superabsorbent polymer and 50 g of physiological saline solution.

Figure 22:
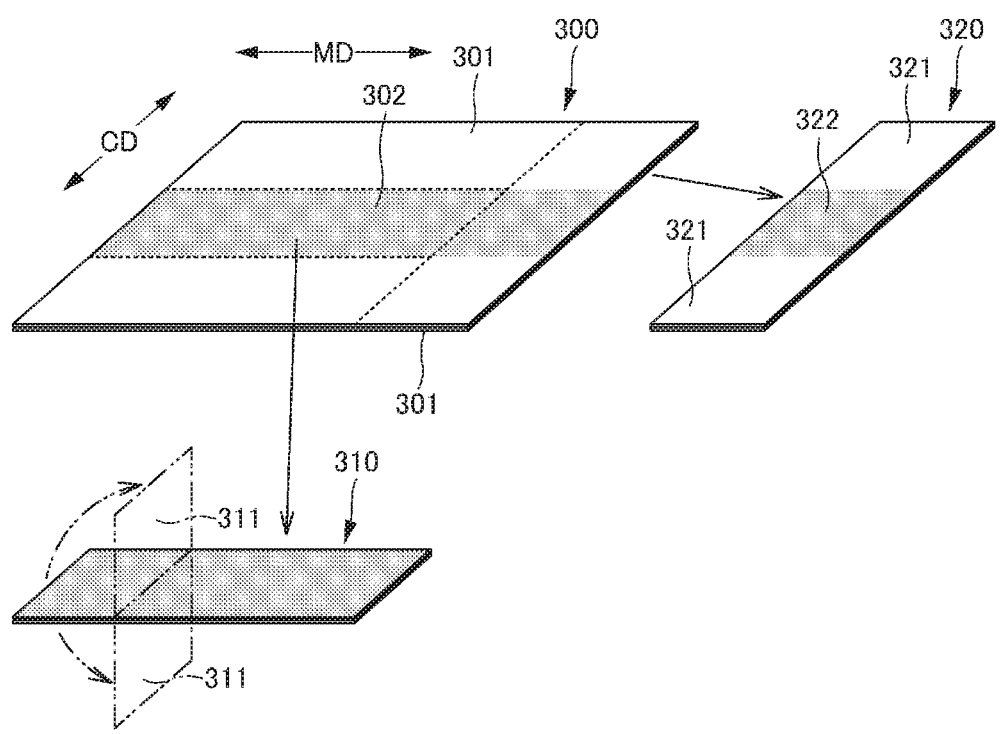
FIG. 22 is an explanatory view of a test piece of a separation strength measurement test.
Figure 23:
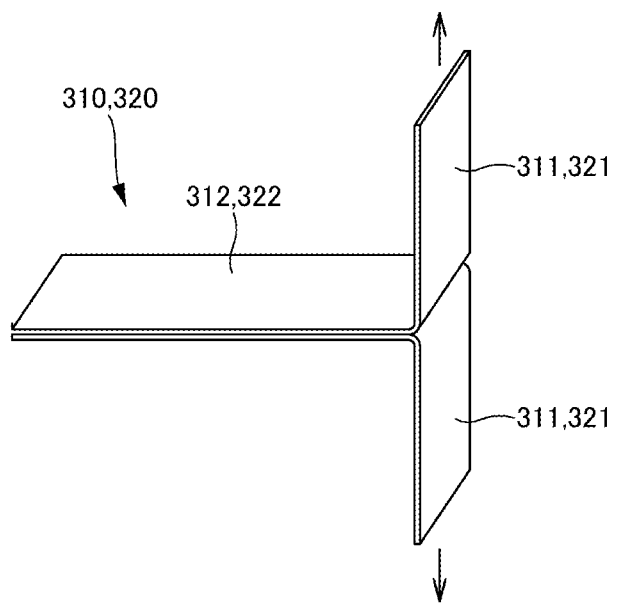
FIG. 23 is an explanatory view of a separation strength measurement test.

"Separation strength" of the hot melt adhesive is measured as follows. That is, two hydrophobic spunbonded nonwoven fabrics 301 formed of PP fibers having the fineness of 1.44 dtex and a basis weight of 17 g/m$^2$ are prepared (MD 100 mm or more×CD 75 mm or more). The hot melt adhesive 302 to be measured is applied to the CD direction center region of one hydrophobic spunbonded nonwoven fabric 301 with the coating amount of 20 g/m$^2$ continuously in the MD with the coating width of 25 mm. After bonding the other hydrophobic spunbonded nonwoven fabric 301 to the one hydrophobic spunbonded nonwoven fabric 301 via the hot melt adhesive 302 while aligning in the MD and the CD, the nonwoven fabric bonded body 300 illustrated in FIG. 22 is prepared by reciprocating once a 2 kg-roller to press-bond the nonwoven fabrics thereon. Next, from this nonwoven fabric bonded body 300, a longitudinal direction test piece 310 and a lateral direction test piece 320 are prepared. That is, the nonwoven fabric bonded body 300 is cut along the cutting line indicated by dotted lines in FIG. 22 to obtain the longitudinal direction test piece 310 in which the entire surface is adhered with 75 mm in the MD×25 mm in the CD, and the lateral direction test piece 320 having the non-adhesive portion 321 of 25 mm from both ends in the CD and 25 mm in the MD and 75 mm in the CD and the adhesive portion 322 of 25 mm in the MD×25 mm in the CD. In the longitudinal direction test piece 310, as indicated by two-dot chain lines in FIG. 22, both nonwoven fabrics at the end of 25 mm from one end in the MD are peeled off (adhesive force of an object to be bonded is lowered by spraying a cold spray to the object) to form a grip margins 311. The grip margin 311 of each nonwoven fabric is gripped with upper and lower grips of a tensile testing machine. As illustrated in FIG. 23, the remaining adhesive portion 312 is peeled off under the conditions of a grip interval of 30 mm and a tensile rate of 300 mm/min, and the tensile force (cN/25 mm) required for peeling is measured. In the lateral direction test piece 320, a test is performed in the same manner as the longitudinal direction test piece 310, except that each nonwoven fabric of the non-adhesive portion 321 at one end in the CD is grasped by the upper and lower grips of the tensile testing machine. The fracture state of the peeled portion is monitored, and at the time of interface fracture (interfacial peeling) and cohesive failure, the average value of tensile force at each point is taken as a measurement value by choosing first five vertices and first five bottom points from a corrugated portion after the start of peeling (after the curve has risen) among the measurement curves with the vertical axis as the tensile force. Also, at the time of the material fracture (fracture of the base material), the maximum value of the tensile force is taken as the measured value. The above measurements are performed three times for each of the longitudinal direction test piece 310 and the lateral direction test piece 320, and the measured values of three times are averaged to obtain the longitudinal separation strength and the lateral separation strength.

Figure 24:
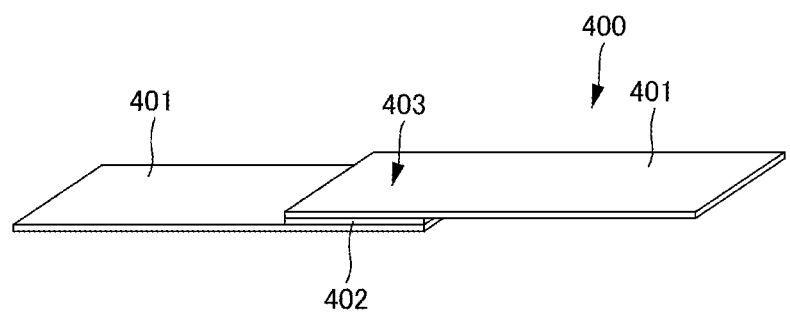
FIG. 24 is an explanatory view of a test piece of a holding power measurement test.
Figure 25:
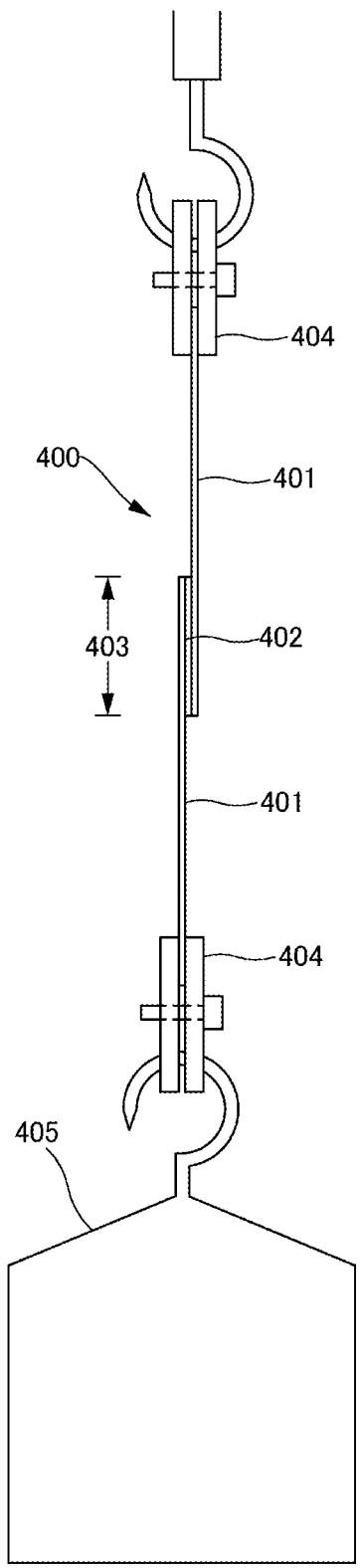
FIG. 25 is an explanatory view of a holding power measurement test.

"Holding power" of the hot melt adhesive is measured as follows. That is, as illustrated in FIG. 24, a PET film having a thickness of 25 μm is prepared, and the end portions in the longitudinal direction (portions of 25 mm from one end in the longitudinal direction) of two rectangular PET films 401 having a length of 100 mm×a width of 25 mm are adhered to each other via the hot melt adhesive layer 402 to be measured to prepare a test piece 400. An adhesive portion 403 of the test piece 400 is 25 mm×25 mm. The hot melt adhesive layer 402 is applied by slot coating at a thickness of 20 g/m$^2$, and after bonding, a 2 kg-roller is reciprocated once from above the adhesive portion 403 and the films 401 are press-bonded. Then the test piece 400 is left under the room temperature (23° C.) for 16 hours. Further, as illustrated in FIG. 25, the PET films 401 at both end portions of the test piece 400 are grasped by grippers 404 which tighten with screws in the thickness direction and left in a creep test machine (constant temperature bath) for two hours at 40° C. such that a force is not applied to the adhesive portion 403. After that, in the creep test machine, as illustrated in FIG. 25, one of the grippers 404 is hung so as to face upward, and a weight 405 is hung on the other gripper 404. A total 1 kg-vertical weight load by the weight 405 and the weight side gripper 404 is applied. The time from start of application of load to the complete separation of the adhesive portion 403 and the peeling-off of the PET film on the side of the weight 405 is measured. The measurement is up to 120 minutes, and when the weight does not fall by the elapse of 120 minutes, the measurement result is "over 120 minutes". The above measurement is performed three times, and the average value of the measurement results is taken as the holding power (minute). As a result of three measurements, when one result is over 120 minutes, and two results are 120 minutes or less, the average value of the two measurement results of 120 minutes or less is used as the holding power. When two results are more than 120 minutes, and one result is 120 minutes or less, the one measurement result of 120 minutes or less is taken as the holding power. When three results are over 120 minutes, the holding power is over 120 minutes.

"Loop tack adhesion" means a value measured as follows. That is, a hot melt adhesive is applied to a PET plate having a thickness of 50 μm at a thickness of 50 μm. This PET plate is cut into a tape having a size of 25 mm in width and 125 mm in length, and then looped by overlapping both ends of the tape. After fixing this loop to the LT-100 type loop tack tester (manufactured by Chem Instrument Co., Ltd.), the loop tape is bonded to a PE (polyethylene) board in an adhesion area of 25 mm×25 mm for an adhesion time of two seconds. Next, a the loop tape is peeled off at 20° C. at a peeling rate of 300 mm/min, and the maximum power is measured. The maximum power is set to the loop tack adhesion.

"Melt viscosity" is measured at a prescribed temperature using a Brookfield B type viscometer (spindle No. 027) in accordance with JIS Z 8803.

When environmental conditions in tests and measurements are not described, the tests and measurements shall be carried out in a test room or apparatus in a standard state (the test location is at a temperature of 20±5° C. and a relative humidity of 65% or less).

The dimension of each part means the dimension in the spread state, not the natural length state, unless otherwise stated.

INDUSTRIAL APPLICABILITY

The present invention is suitable for an underpants-type disposable diaper as in the above example, and applicable to a stretchable structure and a manufacturing method for a general disposable wearing article such as a disposable diaper of a tape type or a pad type as well as a sanitary napkin.

REFERENCE SIGNS LIST 11 liquid impervious sheet
12 outer member
12A side seal portion
12H second sheet layer
12S first sheet layer
12r folded back portion
19 elastic member
20 end portion of stretchable region
200 inner member
21 non-stretchable region
22, 23 stretchable region
22 intermittent stretchable region
23 continuous stretchable region
30 top sheet
40 intermediate sheet
50 absorbent element
56 absorber
58 package sheet
60 three-dimensional gather
62 gather sheet
70 sheet bonded portion
71 first hot melt adhesive
72 second hot melt adhesive
80 pleat
CT cutting position

The invention claimed is:

1. A stretchable structure of a disposable wearing article, the disposable wearing article comprising a first sheet layer, a second sheet layer opposed to one surface of the first sheet layer, and an elastic member provided between the first sheet layer and the second sheet layer,
wherein, a stretchable region and a non-stretchable region are alternately repeated to form three or more regions from one end to the other end in a stretching direction in the stretchable structure, the both ends of the three or more regions being the stretchable regions,
wherein an adhesive region of a hot melt adhesive, where the elastic member is adhered to at least one of the first sheet layer and the second sheet layer, is provided at both ends of the stretchable region in the stretching direction, and
wherein in a spread state, (a) intervals between adhesive regions adjacent in the stretching direction are all of the same length, and (b) the length in the stretching direction of each adhesive region which is positioned between each non-stretchable region and each stretchable region is equal to twice the length in the stretching direction of the adhesive regions positioned at either end of the stretchable structure in the stretching direction.

2. The stretchable structure of a disposable wearing article according to claim 1,
wherein the disposable wearing article is an underpants-type disposable diaper which includes an outer member forming a front body and a back body and an inner member attached to the outer member and containing an absorber, and in which both sides of the outer member in the frond body and both sides of the outer member of the back body are joined to each other, a range in a front-back direction corresponding to the joined portion is an annular lower torso portion, and a waist opening and a pair of right and left leg openings are formed,
in the stretchable structure, the elastic member is provided along a width direction in a lower torso portion of the outer body, and
the non-stretchable region is provided in an intermediate portion in the width direction of the lower torso portion, and the stretchable region is provided on both sides in the width direction of the non-stretchable region.

3. The stretchable structure of a disposable wearing article according to claim 2, wherein the first sheet layer and the second sheet layer are adhered via a hot melt adhesive intermittently disposed at least in the stretching direction, or no hot melt adhesive is provided between the first sheet layer and the second sheet layer, in a region other than the adhesive region of the hot melt adhesive at both end portions in the stretching direction of the stretchable region.

4. The stretchable structure of a disposable wearing article according to claim 1, wherein the first sheet layer and the second sheet layer are adhered via a hot melt adhesive intermittently disposed at least in the stretching direction, or no hot melt adhesive is provided between the first sheet layer and the second sheet layer, in a region other than the adhesive region of the hot melt adhesive at both end portions in the stretching direction of the stretchable region.

5. A method of forming a stretchable structure of a disposable wearing article, comprising:
while continuously conveying a first sheet layer and a second sheet layer in a machine direction, continuously sandwiching an elastic member between the first sheet layer and the second sheet layer in the machine direction, and fixing the elastic member to at least one of the first sheet layer and the second sheet layer; and
after that, repeatedly forming a unit stretchable structure in the machine direction, in which a stretchable region and a non-stretchable region obtained by cutting the elastic member are alternately repeated three or more regions in the machine direction, and both ends in the machine direction become stretchable regions, and cutting the unit stretchable structure into individual stretchable structures at the boundary of the unit stretchable structures adjacent in the machine direction,
wherein, when the elastic member is fixed,
the elastic member is fixed to at least one of the first sheet layer and the second sheet layer via a hot melt adhesive,
wherein application regions of the hot melt adhesive are disposed in each of a portion to be an end portion of a stretchable region of a pair of the unit stretchable structures adjacent in the machine direction and a portion to be an end portion on the non-stretchable region side of the stretchable region,
wherein intervals between application regions adjacent in the are the same, and
wherein the application regions have the same length in the machine direction such that after cutting the unit stretchable structure into individual stretchable structures the length in the machine direction of each adhesive region which is positioned between each non-stretchable region and each stretchable region is equal to twice the length in the machine direction of each adhesive region that is positioned at either end of each of the individual stretchable structures in the machine direction.

6. The method of forming a stretchable structure of a disposable wearing article according to claim 5, wherein the disposable wearing article is an underpants-type disposable diaper which includes an outer member forming a front body and a back body and an inner member attached to the outer member and containing an absorber, and in which both sides of the outer member in the frond body and both sides of the outer member of the back body are joined to each other, a range in a front-back direction corresponding to the joined portion is an annular lower torso portion, and a waist opening and a pair of right and left leg openings are formed, in the stretchable structure, the elastic member is provided along a width direction in a lower torso portion of the outer body, and the non-stretchable region is provided in an intermediate portion in the width direction of the lower torso portion, and the stretchable region is provided on both sides in the width direction of the non-stretchable region.

7. The method of forming a stretchable structure of a disposable wearing article according to claim 6, wherein the first sheet layer and the second sheet layer are adhered via a hot melt adhesive intermittently in the machine direction, or no hot melt adhesive is applied between the first sheet layer and the second sheet layer in a region other than an application region of a portion to be an end portion of a stretchable region of a pair of the unit stretchable structures adjacent in the machine direction and a portion to be an end portion on the non-stretchable region side of the stretchable region.

8. The method of forming a stretchable structure of a disposable wearing article according to claim 5, wherein the first sheet layer and the second sheet layer are adhered via a hot melt adhesive intermittently in the machine direction, or no hot melt adhesive is applied between the first sheet layer and the second sheet layer in a region other than an application region of a portion to be an end portion of a stretchable region of a pair of the unit stretchable structures adjacent in the machine direction and a portion to be an end portion on the non-stretchable region side of the stretchable region.

\* \* \* \* \*